United States Patent
Resconi et al.

(10) Patent No.: US 9,079,985 B2
(45) Date of Patent: Jul. 14, 2015

(54) BRIDGED METALLOCENE CATALYSTS

(75) Inventors: Luigi Resconi, Ferrara (IT); Pascal Castro, Helsinki (FI); Alexander Z. Voskoboynikov, Moscow (RU); Vyatcheslav V. Izmer, Moscow (RU); Dmitry S. Kononovich, Moscow (RU)

(73) Assignee: BOREALIS AG, Vienna (AT)

( * ) Notice: Subject to any disclaimer, the term of this patent is extended or adjusted under 35 U.S.C. 154(b) by 15 days.

(21) Appl. No.: 13/996,831

(22) PCT Filed: Dec. 20, 2011

(86) PCT No.: PCT/EP2011/073426
§ 371 (c)(1),
(2), (4) Date: Sep. 13, 2013

(87) PCT Pub. No.: WO2012/084961
PCT Pub. Date: Jun. 28, 2012

(65) Prior Publication Data
US 2014/0018506 A1    Jan. 16, 2014

(30) Foreign Application Priority Data
Dec. 22, 2010   (EP) ..................................... 10196564

(51) Int. Cl.
| | | |
|---|---|---|
| C08F 4/6592 | (2006.01) | |
| C08F 4/642 | (2006.01) | |
| C08F 4/643 | (2006.01) | |
| C08F 10/00 | (2006.01) | |
| C08F 4/76 | (2006.01) | |
| C08F 4/659 | (2006.01) | |
| B01J 31/22 | (2006.01) | |
| C07F 17/00 | (2006.01) | |
| C08F 4/52 | (2006.01) | |

(Continued)

(52) U.S. Cl.
CPC ............... *C08F 4/76* (2013.01); *B01J 31/2295* (2013.01); *C07F 17/00* (2013.01); *C08F 4/52* (2013.01); *C08F 4/65908* (2013.01); *C08F 4/65927* (2013.01); *C08F 10/00* (2013.01); *B01J 2231/122* (2013.01); *B01J 2531/48* (2013.01); *B01J 2531/49* (2013.01); *C08F 110/06* (2013.01); *C08F 210/06* (2013.01)

(58) Field of Classification Search
CPC .. C08F 4/65927; C08F 4/65912; C08F 10/00; C08F 4/6508; C08F 4/6512; C08F 4/6516; C07F 17/00
USPC ........... 502/103, 152; 526/160, 165, 348, 943
See application file for complete search history.

(56) References Cited

FOREIGN PATENT DOCUMENTS

| EP | 1323747 A1 | 7/2003 |
|---|---|---|
| EP | 1847552 A1 | 10/2007 |

(Continued)

OTHER PUBLICATIONS

A Enders and G. Maas "Advances in Colloid and Interface Science", "Chemie in unserer Zeit", 34. Jahrg. 2000, Nr.6, and of Pierandrea Lo Nostro, 56 (1995) 245-287, Elsevier Science.

(Continued)

*Primary Examiner* — Caixia Lu
(74) *Attorney, Agent, or Firm* — Banner & Witcoff, Ltd.

(57) ABSTRACT

A solid, particulate catalyst comprising: (i) a complex of formula (I) wherein M is zirconium or hafnium; each X is a sigma ligand; L is a divalent bridge selected from —$R'_2C$—, —$R'_2C$—$CR'_2$—, —$R'_2Si$—, —$R'_2Si$—$SiR'_2$—, —$R'_2Ge$—, wherein each R' is independently a hydrogen atom, C1-C20-hydrocarbyl, tri(C1-C20-alkyl)silyl, C6-C20-aryl, C7-C20-arylalkyl or C7-C20-alkylaryl; each $R^1$ is a C4-C20 hydrocarbyl radical branched at the β-atom to the cyclopentadienyl ring, optionally containing one or more heteroatoms belonging to groups 14-16, or is a C3-C20 hydrocarbyl radical branched at the β-atom to the cyclopentadienyl ring where the β-atom is an Si-atom; each $R^{18}$ is a C1-C20 hydrocarbyl radical optionally containing one or more heteroatoms belonging to groups 14-16; each $R^4$ is a hydrogen atom or a $C_{1-6}$-hydrocarbyl radical; each W is a 5 or 6 membered aryl or heteroaryl ring wherein each atom of said ring is optionally substituted with at least one $R^5$ group; each $R^5$ is the same or different and is a C1-C20 hydrocarbyl radical optionally containing one or more heteroatoms belonging to groups 14-16; and optionally two adjacent $R^5$ groups taken together can form a further mono or multicyclic ring condensed to W optionally substituted by one or two groups $R^5$; and each $R^7$ is a C1-C20 hydrocarbyl radical; and (ii) a cocatalyst, preferably comprising an organometallic compound of a Group 13 metal.

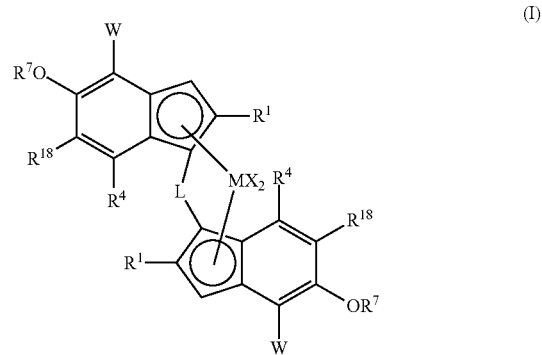

16 Claims, No Drawings

(51) Int. Cl.
*C08F 110/06* (2006.01)
*C08F 210/06* (2006.01)

(56) References Cited

FOREIGN PATENT DOCUMENTS

| WO | 9414856 | A1 | 7/1994 |
|---|---|---|---|
| WO | 9512622 | A1 | 5/1995 |
| WO | 03050131 | A1 | 6/2003 |
| WO | 03051934 | A2 | 6/2003 |
| WO | 2006060544 | A1 | 6/2006 |
| WO | 2006069733 | A1 | 7/2006 |
| WO | 2006097497 | A1 | 9/2006 |
| WO | 2007116034 | A1 | 10/2007 |
| WO | 2009054832 | A1 | 4/2009 |
| WO | 2011135004 | A2 | 11/2011 |

OTHER PUBLICATIONS

G. Singh, A Kothari, V. Gupta, Polymer Testing 2009, 28(5), 475.
Z. Zhou, R. Kuemmerle, X. Qiu, D. Redwine, R. Eong, A Taha, D. Baugh, B. Winniford, J. Mag. Reson. 187 (2007) 225.
V. Busico, P. Carbonniere, R. Cipullo, C. Pellecchia, J. Severn, G. Talarico, Macromol. Rapid Commun. 2007, 28, 1128.
L. Resconi, L. Cavallo, A Fait, F. Piemontesi, Chern. Rev. 2000, 100 (4), 1253.
Cheng,H.N.,Macromolecules 1984,17, 1950.
W-J.Wang and S. Zhu, Macromolecules 2000, 33 1157.
V. Busico and R. Cipullo, Progress in Polymer Science, 2001, 26, 443-533.
C. De Rosa, F. Auriemma, M. Paolillo, L. Resconi, I. Camurati, Macromolecules 2005, 38(22), 9143-9154.
Spaleck W. et al. Organometallics 1994, 13, 954-963.
International Search Report mailed Mar. 27, 2012 (PCT/EP2011/073426); ISA/EP.

BRIDGED METALLOCENE CATALYSTS

The present application is a U.S. National Phase filing of International Application No. PCT/EP2011/073426, filed on Dec. 20, 2011, designating the United States of America and claiming priority to European Patent Application No. 10196564.8, filed Dec. 22, 2010, and this application claims priority to and the benefit of the above-identified applications, which are both incorporated by reference herein in their entireties.

This invention relates to catalysts comprising bridged bis indenyl Π-ligands useful in the formation of olefin polymerisation catalysts, as well as the use thereof in olefin polymerisation, in particular for polymerising propylene and especially propylene copolymers with ethylene. In particular, the invention relates to catalysts which comprise certain bridged bis indenyl complexes in solid form. e.g. supported or ideally in solid but unsupported form. Certain complexes of the invention are also new and form still yet further aspects of the invention.

Metallocene catalysts have been used to manufacture polyolefins for many years. Countless academic and patent publications describe the use of these catalysts in olefin polymerisation. Metallocenes are now used industrially and polyethylenes and polypropylenes in particular are often produced using cyclopentadienyl based catalyst systems with different substitution patterns.

These metallocenes can be used in solution polymerisation but results of such polymerisations have generally been poor. These metallocenes are therefore conventional supported on a carrier such as silica. Research has found that heterogeneous catalysis (in which the catalyst particles do not dissolve in the reaction medium) gives rise to better polymer products than homogeneous catalysis (in solution). The use therefore of a support is common place. Despite several years of development of this catalyst technology, there is still room for improved activity, and improved polymer particle formation.

In WO03/051934, the inventors proposed an alternative form of catalyst which is provided in solid form but does not require a conventional external carrier material such as silica. The invention is based on the finding that a homogeneous catalyst system containing an organometallic compound of a transition metal can be converted, in a controlled way, to solid, uniform catalyst particles by first forming a liquid/liquid emulsion system, which comprises as the dispersed phase, said solution of the homogeneous catalyst system, and as the continuous phase a solvent immiscible therewith, and then solidifying said dispersed droplets to form solid particles comprising the said catalyst.

The invention described in WO03/051934 enabled the formation of solid spherical catalyst particles of said organotransition metal catalyst without using e.g. external porous carrier particles, such as silica, normally required in the art. Thus, problems relating to catalyst silica residues can be solved by this type of catalyst. Further, it could be seen that catalyst particles having improved morphology, will give, due to the replica effect, polymer particles having improved morphology as well.

Although a lot of work has been done in the field of metallocene catalysts, both with conventional supported catalysts as well with solid catalysts prepared according to the principles as described in said WO03/051934, there still remain some problems, which relate especially to the productivity or activity of the catalysts. The productivity or activity has been found to be relatively low, especially when polymers of low melt index (MI) (i.e. high molecular weight, $M_w$) are produced using known catalysts.

There remains a need therefore to find new catalysts for olefin polymerisation, which are able to produce polymers with desired properties and which have high activity and/or productivity. Further, it is highly desired in many polymer applications that inorganic residues, e.g. silica residues, in the final product are reduced as much as possible.

A further problem relating to the catalyst activity seems to be that activity of known catalysts is not at a sufficiently high level over a broad range of hydrogen concentration, i.e. where the skilled man is producing lower or higher Mw polymers. Thus, catalysts having broader operating windows, i.e. good activity over a broad range of molecular weights of the polymer, are highly desired. Further, the problems with conventional silica supported catalysts, i.e. low productivity, have to be avoided. Producing polymers with high isotacticity and hence higher crystallinity and thermal resistance is also desirable.

In particular, the present inventors were faced with the problem of manufacturing a polymer with high molecular weight (i.e. enabling the formation of polymer components with low melt index). This had to be achieved whilst maintaining high catalyst activity and productivity.

As a consequence, the inventors set out to develop a catalyst having a superior polymerisation behaviour than the above mentioned polymerisation catalyst systems regarding one or more of the following characteristics:
  improved performance towards high molecular weight propylene homo polymers having low melting temperatures and still low xylene solubles
  improved performance towards high molecular weight propylene copolymers
  improved productivity in producing propylene copolymers
  obtaining propylene copolymers with low xylene solubles even in the presence of relatively high amount of comonomer.

The present inventors have now found a new class of olefin polymerisation catalysts, which are able to solve the problems disclosed above, and which catalysts are not previously described in the art. The invention combines known supporting techniques, for example using silica as described in WO2006/097497, or the catalyst emulsion/solidification techniques of WO03/051934 with a specific group of metallocene complexes based on a bis-indenyl structure in which the 2-position of the indenyl ring must carry a group, branched at the β carbon to the cyclopentadienyl ring. This combination surprisingly results in catalysts having high activity, e.g. improved activity over the known catalysts prepared according to WO03/051934. Moreover, the features of the catalyst of the invention enable the formation of polymers having a broad range of molecular weights, especially, very high molecular weight products. Further, as a special embodiment, the invention further provides a catalyst, where no silica support material need be used. This avoids any problems relating to the use of the conventional supported catalysts, such as silica supported catalysts.

These polymers operate well over a broad range of hydrogen pressures, and form advantageous polymers.

The inventors have also found that the new catalyst described herein is ideal for the production of random propylene/ethylene copolymers with increased molecular weight. This can be achieved with high productivity and high catalyst activity. Moreover, and surprisingly, the propylene-rich copolymers formed using the catalyst of the present invention exhibit decreasing melt index with increasing ethylene concentration. Furthermore, the xylene soluble content of the polymers remains low indicating even comonomer distribution.

Complexes similar to those used in the manufacture of the catalysts of the invention are disclosed in the prior art but they do not show the same advantageous combination of improved properties. Moreover, the importance of the branch at the β-position of the substituent on the 2-position of the indenyl ligand is not appreciated, in particular in combination with the alkoxy type group at the 5-position of the indenyl ring. Moreover, the complexes of the invention generally represent a selection from the very broad disclosures of metallocene catalysts in the prior art.

WO2009/054832 discloses conventionally supported metallocene catalysts which are branched at the 2-position of the cyclopentadienyl ring in at least one of the ligands making up the catalyst. In the examples, the 6-membered portion of the indenyl rings remain unsubstituted however.

WO2007/116034 describes metallocene compounds substituted in the 2-position by a linear alkyl group. In particular the compound dimethylsilyl(2-methyl-4-phenyl-5-methoxy-6-tertbutylinden-1-yl dichlorozirconium is described which carries a methyl group at the 2-position.

It has now surprisingly been found that using the particular complexes described below in solid form the resulting catalysts comprehensively outperform known catalysts prepared according to the method of WO03/051934.

Thus, viewed from one aspect the invention provides a solid particulate catalyst comprising:
(i) a complex of formula (I):

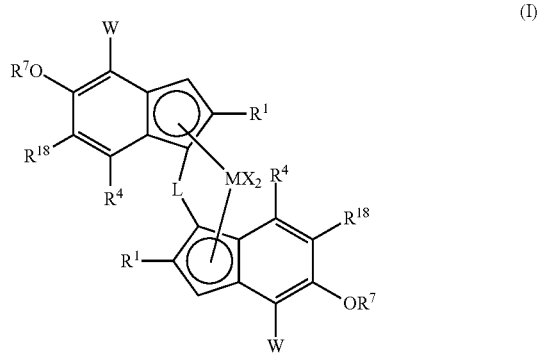

(I)

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-hydrocarbyl, tri(C1-C20-alkyl)silyl, C6-C20-aryl, C7-C20-arylalkyl or C7-C20-alkylaryl;
each $R^1$ is a C4-C20 hydrocarbyl radical branched at the β-atom to the cyclopentadienyl ring, optionally containing one or more heteroatoms belonging to groups 14-16, or is a C3-C20 hydrocarbyl radical branched at the β-atom to the cyclopentadienyl ring where the β-atom is an Si-atom;
each $R^{18}$ is a C1-C20 hydrocarbyl radical optionally containing one or more heteroatoms belonging to groups 14-16;
each $R^4$ is a hydrogen atom or a $C_{1-6}$-hydrocarbyl radical;
each W is a 5 or 6 membered aryl or heteroaryl ring wherein each atom of said ring is optionally substituted with at least one $R^5$ group;
each $R^5$ is the same or different and is a C1-C20 hydrocarbyl radical optionally containing one or more heteroatoms belonging to groups 14-16; and optionally two adjacent $R^5$ groups taken together can form a further mono or multicyclic ring condensed to W optionally substituted by one or two groups $R^5$; and
each $R^7$ is a C1-C20 hydrocarbyl radical;
and (ii) a cocatalyst, preferably comprising an organometallic compound of a Group 13 metal.

The catalyst of the invention is in solid particulate form either supported on an external carrier material, like silica or alumina, or, in a particularly preferred embodiment, is free from an external carrier. Ideally, the catalyst is obtainable by a process in which
(a) a liquid/liquid emulsion system is formed, said liquid/liquid emulsion system comprising a solution of the catalyst components (i) and (ii) dispersed in a solvent so as to form dispersed droplets; and
(b) solid particles are formed by solidifying said dispersed droplets.

Viewed from another aspect the invention provides a process for the manufacture of a catalyst as hereinbefore defined comprising obtaining a complex of formula (I) and a cocatalyst as hereinbefore described;
forming a liquid/liquid emulsion system, which comprises a solution of catalyst components (i) and (ii) dispersed in a solvent, and solidifying said dispersed droplets to form solid particles.

Viewed from another aspect the invention provides the use in olefin polymerisation of a catalyst as hereinbefore defined, especially for propylene polymerisation, and still more especially for the formation of a random copolymer, in particular of propylene and most especially of ethylene and propylene.

Viewed from another aspect the invention provides a process for the polymerisation of at least one olefin comprising reacting said at least one olefin with a catalyst as hereinbefore described, especially for propylene polymerisation, and still more especially for the formation of a random propylene copolymer, in particular a random propylene/ethylene copolymer comprising polymerising propylene and at least one C2-10 alpha olefin (especially ethylene) in the presence of said catalyst.

DEFINITIONS

Throughout the description the following definitions are employed.

By free from an external carrier is meant that the catalyst does not contain an external support, such as an inorganic support, for example, silica or alumina, or an organic polymeric support material.

The term $C_{1-20}$ hydrocarbyl group therefore includes $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl groups, $C_{7-20}$ alkylaryl groups or $C_{7-20}$ arylalkyl groups or of course mixtures of these groups such as cycloalkyl substituted by alkyl.

Unless otherwise stated, preferred $C_{1-20}$ hydrocarbyl groups are $C_{1-20}$ alkyl, $C_{4-20}$ cycloalkyl, $C_{5-20}$ cycloalkylalkyl groups, $C_{7-20}$ alkylaryl groups, $C_{7-20}$ arylalkyl groups or $C_{6-20}$ aryl groups, especially $C_{1-10}$ alkyl groups, $C_{6-10}$ aryl groups, or $C_{7-12}$ arylalkyl groups, e.g. $C_{1-8}$alkyl groups. Most especially preferred hydrocarbyl groups are methyl, ethyl, propyl, isopropyl, tertbutyl, isobutyl, $C_{5-6}$-cycloalkyl, cyclohexylmethyl, phenyl or benzyl.

The term halo includes fluoro, chloro, bromo and iodo groups, especially chloro groups, when relating to the complex definition.

The term heterocyclic group means a preferably monocyclic non aromatic ring structure comprising at least one heteroatom, e.g. piperidinyl or piperazinyl.

The term heteroaryl means a preferably monocyclic aromatic ring structure comprising at least one heteroatom. Preferred heteroaryl groups have 1 to 4 heteroatoms selected from O, S and N. Preferred heteroaryl groups include furanyl, thiophenyl, oxazole, thiazole, isothiazole, isooxazole, triazole and pyridyl.

Any group including "one or more heteroatoms belonging to groups 14-16" preferably means O, S or N. N groups may present as —NH— or —NR"— where R" is C1-10 alkyl. There may, for example, be 1 to 4 heteroatoms.

The oxidation state of the metal ion is governed primarily by the nature of the metal ion in question and the stability of the individual oxidation states of each metal ion.

It will be appreciated that in the complexes of the invention, the metal ion M is coordinated by ligands X so as to satisfy the valency of the metal ion and to fill its available coordination sites. The nature of these σ-ligands can vary greatly.

Catalyst activity is defined in this application to be the amount of polymer produced/g catalyst/h. Catalyst metal activity is defined here to be the amount of polymer produced/g Metal/h. The term productivity is also sometimes used to indicate the catalyst activity although herein it designates the amount of polymer produced per unit weight of catalyst.

DETAILED DESCRIPTION OF INVENTION

The complexes and hence catalysts of the invention are based on formula (I) as hereinbefore defined which, inter alia, combines the use of the indenyl ring structure with a substituent at the 2-position that is branched β to the cyclopentadienyl ring.

The two multicyclic ligands making up the complex of formula (I) are preferably identical and hence the complex of formula (I) may be symmetrical. The complexes of the invention may be in their meso or racemic forms (or a mixture thereof). Preferably, the racemic (rac) form is used.

M is preferably Zr or Hf, especially Zr.

Each X, which may be the same or different, is preferably a hydrogen atom, a halogen atom, a R, OR, $OSO_2CF_3$, OCOR, SR, $NR_2$ or $PR_2$ group wherein R is a linear or branched, cyclic or acyclic, C1-C20-alkyl, C2-C20 alkenyl, C2-C20 alkynyl, C6-C20-aryl, C7-C20-alkylaryl or C7-C20-arylalkyl radical; optionally containing heteroatoms belonging to groups 14-16. R is preferably C1-10 alkyl or C6-20 aryl. R is more preferably a $C_{1-6}$alkyl, phenyl or benzyl group.

Most preferably each X is independently a hydrogen atom, a halogen atom, $C_{1-6}$-alkoxy group or an R group, e.g. preferably a $C_{1-6}$-alkyl, phenyl or benzyl group. Most preferably X is chlorine or a methyl radical. Preferably both X groups are the same.

L is preferably a bridge comprising a heteroatom, such as silicon or, germanium, e.g. —$SiR^6_2$—, wherein each $R^6$ is independently C1-C20-alkyl, C6-C20-aryl or tri(C1-C20-alkyl)silyl-residue, such as trimethylsilyl. More preferably $R^6$ is a $C_{1-8}$ alkyl, e.g. $C_{1-6}$-alkyl, especially methyl. Most preferably, L is a dimethylsilyl or diethyl bridge.

$R^1$ is branched β to the cyclopentadienyl ring. By branched β to the cyclopentadienyl ring is meant that the second atom from the cyclopentadienyl ring must be secondary or tertiary, preferably secondary. This atom is preferably Si or C but is most preferably C. The $R^1$ radical preferably comprises at least 4 carbon atoms in the chain. Where an Si atom is present β to the cyclopentadienyl ring it is possible for there to be three carbon atoms present in the $R^1$ group in addition to the Si atom at the beta position.

It will also be appreciated that where a cyclic group such as a cycloalkyl group, heterocyclic, heteroaryl or aryl group is present at the atom β to the cyclopentadienyl then there is a branch present.

The $R^1$ group may contain one or more heteroatoms belonging to groups 14-16, e.g. O, N or S. There may be 1 to 3 of such heteroatoms. These heteroatoms may be positioned to allow formation of a heterocyclic or heteroaryl group in the $R^1$ group e.g. a $CH_2$-heteroaryl or $CH_2$-heterocyclic group having 3-10 carbon atoms and one to three heteroatoms.

It is preferred that heteroatoms in the $R^1$ group (other than Si at the beta position as discussed below) are not positioned at the atoms α or β, to the cyclopentadienyl ring. Thus, the backbone atom positioned α to the ring is preferably C, the backbone atom β to the ring is C or Si and the atoms attached to β position (other than hydrogen) are C atoms. Heteroatoms, if present should be positioned at least delta to the cyclopentadienyl ring. Preferably there are no heteroatoms present in groups $R^1$.

Where there is an Si atom β to the cyclopentadienyl ring it is preferred if there are no other heteroatoms present in the $R^1$ group. Where Si interrupts the carbon chain β to the cyclopentadienyl ring, preferred such groups include $CH_2$—$SiR^{10}_3$ where $R^{10}$ is a $C_{1-6}$alkyl group, e.g. methyl.

Preferably $R^1$ is a C4-20 hydrocarbyl group, more preferably C4-C12 hydrocarbyl branched β to the cyclopentadienyl ring, optionally containing one or more heteroatoms belonging to groups 14-16.

Radical $R^1$ is preferably a suitably branched C4-C20-alkyl, a $CH_2$-cycloalkyl group having 4 to 12 carbon atoms or a $CH_2$-aryl radical containing from 7 to 11 carbon atoms.

In a preferred embodiment, $R^1$ is the group —$CH_2$—$R^{1'}$, i.e. the link to the cyclopentadienyl ring is via a methylene group and $R^{1'}$ represents the remainder of the $R^1$ group, e.g. a C3-19 hydrocarbyl group optionally containing one or more heteroatoms belonging to groups 14-16 or a C2-19 hydrocarbyl group where the atom β to the cyclopentadienyl ring is Si.

In particular, $R^{1'}$ represents a $C_{3-7}$-cycloalkyl group (optionally substituted by $C_{1-6}$-alkyl), a $C_{6-10}$-aryl group, especially phenyl or an $C_{3-8}$-alkyl group (such that the beta position to the cyclopentadienyl is branched). In some embodiments the $R^{1'}$ group can represent a heteroaryl or heterocyclic group having 2 to 8 carbon atoms and one to three heteroatoms (e.g. S, N or O). Heteroatoms, if present, should preferably be positioned at least delta to the cyclopentadienyl ring.

Suitable heteroaryl groups include pyrrolyl, indolyl, furanyl, oxazole, thiazole, isothiazole, isooxazole, triazole and pyridyl. Suitable heterocyclic groups include piperidinyl and piperazinyl.

In a further preferred embodiment therefore, $R^1$ is a group $CH_2$—$C(R_3)_{3-q}(H)_q$ wherein each $R_3$ is a $C_{1-6}$-alkyl group or together two $R_3$ groups form a $C_{3-7}$-cycloalkyl ring. The subscript q can be 1 or 0.

More preferably $R^1$ is a suitably branched $C_{4-10}$-alkyl radical, preferably a suitably branched $C_{4-8}$-alkyl radical. $R^1$ is ideally an isobutyl, —$CH_2C(Me)_3$ or —$CH_2CH(Me)(Et)$ group. Alternatively, $R^1$ is —$CH_2C_6H_{11}$ where $C_6H_{11}$ is cyclohexyl, $CH_2C_6H_{11}$(Me) where the cyclohexyl is substituted by methyl or —$CH_2C_6H_5$ (benzyl).

Preferably $R^{18}$ is branched, cyclic or acyclic, $C_{3-20}$ alkyl, $C_{3-20}$ alkenyl, $C_{3-20}$ alkynyl, C6-C20-aryl, C7-C20-alkylaryl or C7-C20-arylalkyl radical, optionally containing one or more heteroatoms belonging to groups 14-16. It is preferred however if $R^{18}$ is free of heteroatoms. Preferably $R^{18}$ is a $C_{3-10}$ alkyl.

Preferably $R^{18}$ is a C4-C10 branched alkyl or is an alkyl-cycloalkyl group. Preferred options include, tert-butyl, 1-alkylcyclopentyl or 1-alkylcyclohexyl.

$R^4$ is preferably a hydrogen atom or $C_{1-6}$ alkyl such as methyl, ethyl, propyl or isopropyl group, most preferably methyl or especially hydrogen.

W is preferably an optionally substituted phenyl group, or a 5 or 6 membered heteroaryl group such as a furanyl, thiophenyl, pyrrolyl, triazolyl, and pyridyl.

Any five membered heteroaryl group should preferably comprise one heteroatom in the ring, such as O, N or S.

Preferably W is a phenyl derivative. More preferably the phenyl derivative is unsubstituted or carries one to three substituents. The optional substituent on any W group is $R^5$. If present, there should be 1 to 3 $R^5$ groups, preferably one or two $R^5$ groups.

Preferably $R^5$ is a linear or branched, cyclic or acyclic, C1-C20-alkyl, C2-C20 alkenyl, C2-C20 alkynyl, C6-C20-aryl, C7-C20-alkylaryl or C7-C20-arylalkyl radical optionally containing one or more heteroatoms belonging to groups 14-16. Preferably $R^5$ is a linear or branched, cyclic or acyclic, C1-C10-alkyl group. Most preferably $R^5$ is a tert-butyl group.

It is preferred that any $R^5$ group present is located at 3, 4 and/or 5 position to the bond to the indenyl group.

In one preferred embodiment two adjacent $R^5$ groups taken together can form a further mono or multicyclic ring condensed to W. The new ring is preferably 5 or 6 membered or the $R^5$ groups preferably form two new rings such as one further five membered and six membered ring.

The new ring or rings can be aliphatic or aromatic. Preferably any new ring forms an aromatic system with the W ring to which it is attached.

In this way groups such as indolyl, carbazolyl, benzothiophenyl and naphthyl can be formed at position W. It is also within the scope of the invention for these new rings to be substituted by 1 or 2 $R^5$ groups (in which the option of two adjacent $R_5$ groups forming another ring is excluded).

In a most preferred embodiment, W is a phenyl group carrying one or two $R^5$ substituents or is simply a phenyl group. When present, that substituent(s) is also preferably a $C_{1-10}$-alkyl radical.

$R^7$ is preferably a C1-10 hydrocarbyl group, more preferably a $C_{1-10}$ alkyl or $C_{6-20}$ aryl group, especially a $C_{1-6}$ alkyl. The use of methyl or ethyl is most preferred.

In a preferred embodiment therefore the complex of the invention is of formula (II)

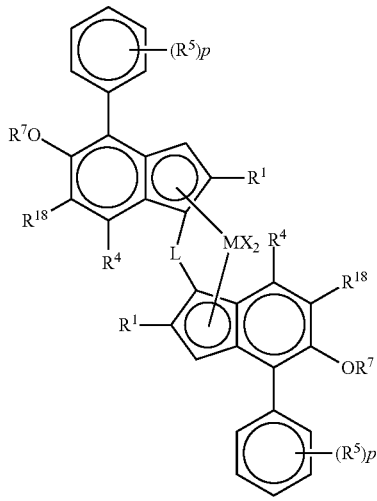

(II)

wherein
M is Zr or Hf;
each $R^1$ is $CH_2$-Ph, $CH_2$—$C(R^3)_{3-q}(H)_q$ wherein $R^3$ is a $C_{1-6}$-alkyl group or together two $R^3$ groups form a $C_{3-7}$-cycloalkyl ring wherein said ring is optionally substituted by a $C_{1-6}$alkyl group and q can be 1 or 0;

L is $SiR^6_2$;

$R^6$ is C1-10 alkyl, $C_{6-10}$-aryl, $C_{7-12}$-alkylaryl, or $C_{7-12}$-arylalkyl;

each X is a hydrogen atom, benzyl, OR, a halogen atom, or an R group;

R is $C_{1-10}$ alkyl or $C_{6-20}$ aryl;

each $R^4$ is H or $C_{1-3}$-alkyl;

p is 0 to 2;

$R^5$ is $C_{1-10}$-alkyl;

$R^7$ is $C_{1-10}$ alkyl; and $R^{18}$ is $C_{1-10}$-alkyl;

and wherein the two ligands forming the complex are identical.

In a still further preferred embodiment, the invention provides a complex of formula (III)

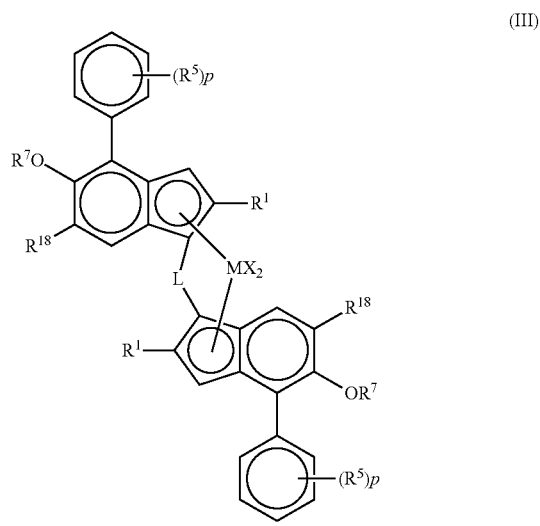

(III)

in which:

M is Zr;

each $R^1$ is $CH_2$-Ph, $CH_2$—$C(R^3)_{3-q}(H)_q$ wherein $R^3$ is a $C_{1-6}$-alkyl group or together two $R^3$ groups form a $C_{3-7}$-cycloalkyl ring wherein said ring is optionally substituted by a $C_{1-6}$alkyl group and q can be 1 or 0;

L is $SiR^6_2$;

$R^6$ is $C_{1-8}$ alkyl;

each X is a halogen atom, methoxy, benzyl or methyl;

p is 0 or 1;

$R^7$ is $C_{1-6}$ alkyl;

$R^{18}$ is $C_{3-10}$ alkyl; and $R^5$ is $C_{1-6}$ alkyl;

and wherein the two ligands forming the complex are identical.

In a further highly preferred embodiment, the invention provides a complex of formula (IV)

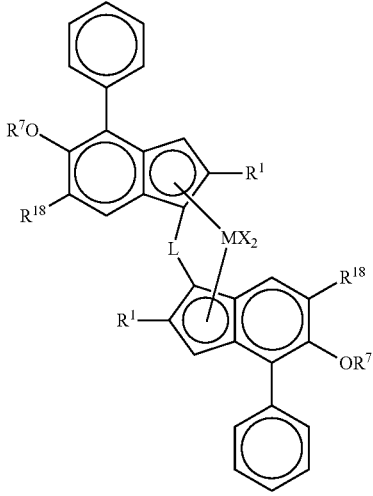

(IV)

wherein L is SiR$^6{}_2$;
R$^6$ is C$_{1-8}$ alkyl;
R$^1$ is CH$_2$-Ph, CH$_2$—C(R$^3$)$_{3-q}$(H)$_q$ wherein R$^3$ is a C$_{1-6}$-alkyl group or together two R$^3$ groups form a C$_{3-7}$-cycloalkyl ring wherein said ring is optionally substituted by a C$_{1-6}$alkyl group and q can be 1 or 0;
each X is a halogen atom, methoxy, benzyl or methyl;
M is Zr;
R$^7$ is C$_{1-6}$ alkyl; and
R$^{18}$ is C$_{3-10}$ alkyl;
and wherein the two ligands forming the complex are identical.

A still further especially preferred complex of the invention is of formula (V)

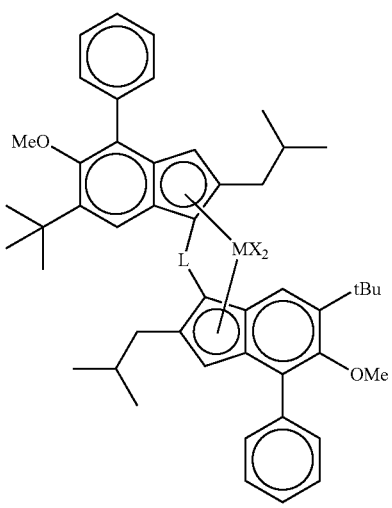

(V)

wherein L is SiR$^6{}_2$;
R$^6$ is C$_{1-8}$ alkyl;
each X is a halogen atom, methoxy, benzyl or methyl; and M is Zr; most especially

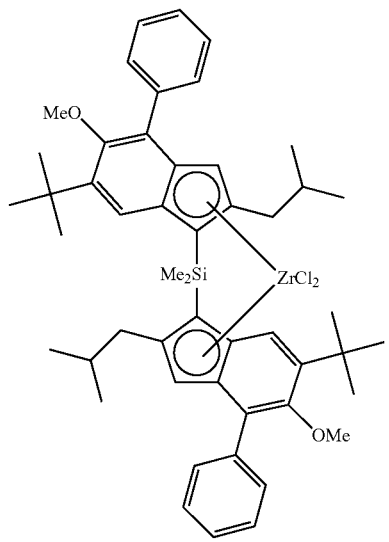

In a further embodiment, the invention provides new complexes. In particular, the invention provides complexes of formula (VI) and of formula (VII)

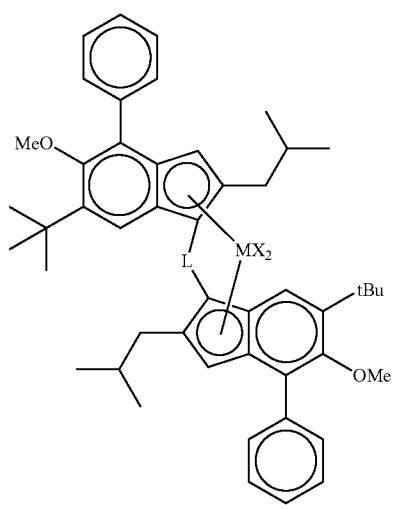

(VI)

wherein M is Zr or Hf;
L is SiR$^6{}_2$;
R$^6$ is C1-10 alkyl, C$_{6-10}$-aryl, C$_{7-12}$-alkylaryl, or C$_{7-12}$-arylalkyl;
each X is a hydrogen atom, benzyl, OR, a halogen atom, or an R group; and
R is C$_{1-10}$ alkyl or C$_{6-20}$ aryl.
or (VII)

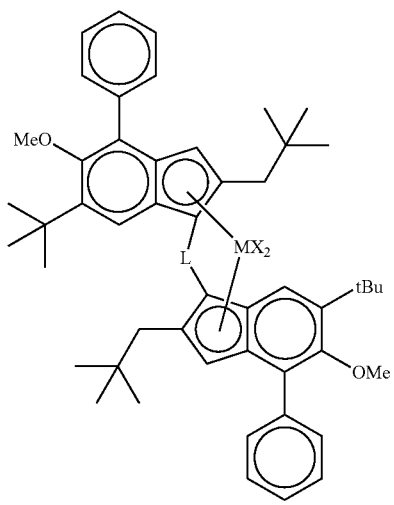

wherein M is Zr or Hf;
L is $SiR^6{}_2$;
$R^6$ is C1-10 alkyl, $C_{6-10}$-aryl, $C_{7-12}$-alkylaryl, or $C_{7-12}$-arylalkyl;
each X is a hydrogen atom, benzyl, OR, a halogen atom, or an R group; and
R is $C_{1-10}$ alkyl or $C_{6-20}$ aryl.

Furthermore, it is submitted that the ligand precursors of formulas (VI) and (VII) are also new and form a further aspect of the invention. The ligand precursors do not contain the $MX_2$ group and the indenyl ring is not deprotonated. Thus, the invention covers compounds of formula (VIII) and (IX) and their double bond isomers:

(VIII)

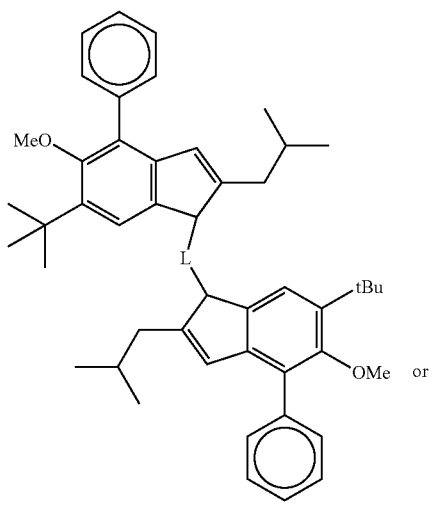

or (IX)

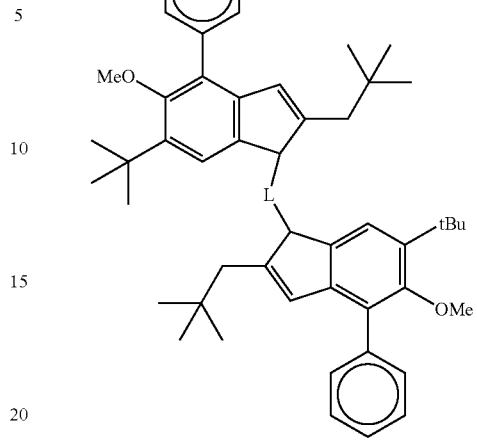

wherein L is $SiR^6{}_2$;
$R^6$ is C1-10 alkyl, $C_{6-10}$-aryl, $C_{7-12}$-alkylaryl, or $C_{7-12}$-arylalkyl.

It is preferred in the ligands of formula (VI) to (IX) that L is $SiR^6{}_2$;

$R^6$ is $C_{1-8}$ alkyl;

each X is a halogen atom, methoxy, benzyl or methyl; and

M is Zr.

For the avoidance of doubt, any narrower definition of a substituent offered above in connection with any formula can be combined with any other broad or narrow definition of any other substituent.

Throughout the disclosure above, where a narrower definition of a substituent is presented, that narrower definition is deemed disclosed in conjunction with all broader and narrower definitions of other substituents in the application.

Synthesis

The ligands required to form the catalysts of the invention can be synthesised by any process and the skilled organic chemist would be able to devise various synthetic protocols for the manufacture of the necessary ligand materials. WO2007/116034 and the other prior art references mentioned above disclose the necessary chemistry and are herein incorporated by reference.

Schemes summarise a possible synthetic route:

Route

Scheme 1

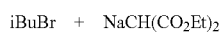

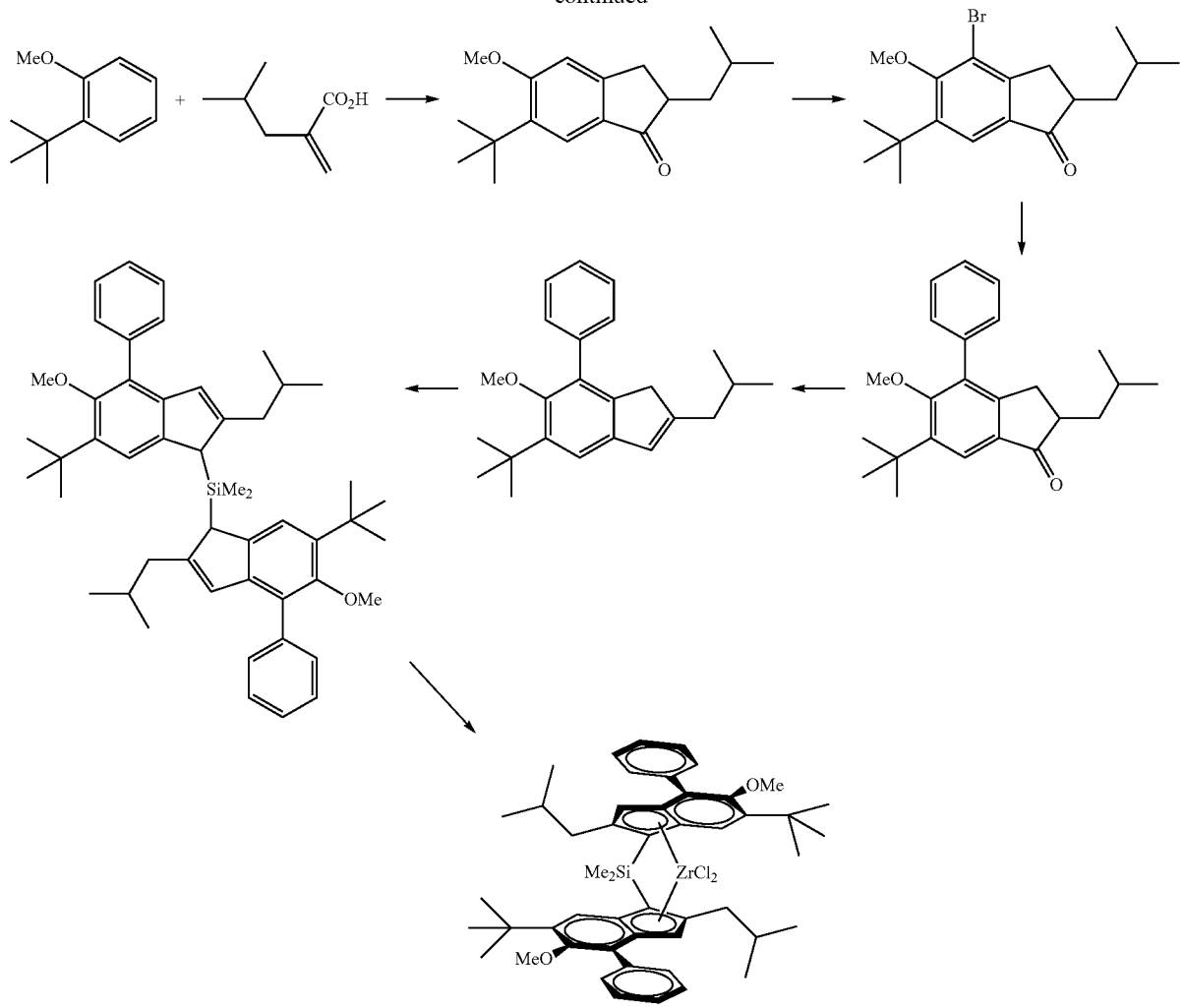

The bis-indenyl ligand of formula (VIII) can be prepared following a synthetic strategy as outlined in Scheme 1. The key intermediate, the 6-tert-butyl-2-isobutyl-5-methoxyindan-1-one, was prepared by acylation of 2-tert-butylanisol with 2-isobutylacrylic acid followed by Nazarov cyclisation. Subsequent bromination, cross-coupling reaction with sodium tetraphenyl borate and reduction/dehydration of the obtained indanone gave the 5-tert-butyl-2-isobutyl-6-methoxy-7-phenyl-1H-indene. Reaction of its lithium salt with dichlorodimethylsilane produced the actual ligand bis(6-tert-butyl-2-isobutyl-5-methoxy-4-phenyl-1H-inden-1-yl)(dimethyl)silane in almost quantitative yield.

The dimethylsilyl-bis(2-isobutyl-4-phenyl-5-methoxy-6-tert-butylinden-1-yl)zirconium dichloride metallocene can then be generated by transmetalation of the dilithium salt of the ligand with zirconium tetrachloride in toluene.
Scheme 2

Preparation of ligand of formula (IX) was analogous for the ligand of formula (VIII), however using as starting material 2-(2,2-dimethylpropyl)acrylic acid instead of 2-isobutylacrylic acid. Detailed preparation is disclosed in the experimental part.
Cocatalyst To form an active catalytic species it is normally necessary to employ a cocatalyst as is well known in the art. Cocatalysts comprising an organometallic compound of Group 13 metal, like organoaluminium compounds used to activate metallocene catalysts are suitable for use in this invention.

The olefin polymerisation catalyst system of the invention comprises (i) a complex in which the metal ion is coordinated by a ligand of the invention; and normally (ii) an aluminium alkyl compound (or other appropriate cocatalyst), or the reaction product thereof. Thus the cocatalyst is preferably an alumoxane, like MAO or an alumoxane other than MAO.

Alternatively, however, the catalysts of the invention may be used with other cocatalysts, e.g. boron compounds such as $B(C_6F_5)_3$, $C_6H_5N(CH_3)_2H:B(C_6F_5)_4$, $(C_6H_5)_3C:B(C_6F_5)_4$ or $Ni(CN)_4[B(C_6F_5)_3]_4{}^{2-}$.

The use of aluminoxanes, especially MAO, is highly preferred.

Suitable amounts of cocatalyst will be well known to the skilled man. Typically Al to M molar ratios are from 1:1 to 1000:1 mol/mol. Preferably when an aluminium alkyl is used as a coctalyst, the molar ratio of the aluminium in the activator to the transition metal in the complex is from 1 to 500 mol/mol, preferably from 10 to 400 mol/mol and in particular from 50 to 400 mol/mol.
Manufacture The metallocene complex of the present invention can be used in combination with a suitable cocatalyst as a catalyst for the polymerization of olefins, e.g. in a solvent such as toluene or an aliphatic hydrocarbon, (i.e. for polymerization in solution), as it is well known in the art. Preferably, polymerization of olefins, especially propylene, takes place in the condensed phase or in gas phase.

The catalyst of the invention is preferably in solid particulate form, e.g. as obtained for example by supporting on an inert organic or inorganic carrier, such as for example silica or in solid particulate form but unsupported.

The particulate support material used is preferably an organic or inorganic material, such as silica, alumina or zirconia or a mixed oxide such as silica-alumina, in particular silica, alumina or silica-alumina.

Especially preferably the support is a porous material so that the complex may be loaded into the pores of the support, e.g. using a process analogous to those described in WO94/14856 (Mobil), WO95/12622 (Borealis) and WO2006/097497. The particle size is not critical but is preferably in the range 5 to 200 μm, more preferably 20 to 80 μm. The use of these supports is routine in the art.

In one particular embodiment, no external carrier is used. In order to provide the catalyst of the invention in solid form but without using an external carrier, it is preferred if a liquid emulsion system is used. The process involves forming dispersing catalyst components (i) and (ii) in a solvent, and solidifying said dispersed droplets to form solid particles.

In particular, the method involves preparing a solution of one or more catalyst components; dispersing said solution in an solvent to form an emulsion in which said one or more catalyst components are present in the droplets of the dispersed phase; immobilising the catalyst components in the dispersed droplets, in the absence of an external particulate porous support, to form solid particles comprising the said catalyst, and optionally recovering said particles.

This process enables the manufacture of active catalyst particles with improved morphology, e.g. with a predetermined spherical shape and particle size and without using any added external porous support material, such as an inorganic oxide, e.g. silica. Also desirable surface properties can be obtained.

By the term "preparing a solution of one or more catalyst components" is meant that the catalyst forming compounds may be combined in one solution which is dispersed to the immiscible solvent, or, alternatively, at least two separate catalyst solutions for each part of the catalyst forming compounds may be prepared, which are then dispersed successively to the solvent.

In a preferred method for forming the catalyst at least two separate solutions for each or part of said catalyst may be prepared, which are then dispersed successively to the immiscible solvent.

More preferably, a solution of the complex comprising the transition metal compound and the cocatalyst is combined with the solvent to form an emulsion wherein that inert solvent forms the continuous liquid phase and the solution comprising the catalyst components forms the dispersed phase (discontinuous phase) in the form of dispersed droplets. The droplets are then solidified to form solid catalyst particles, and the solid particles are separated from the liquid and optionally washed and/or dried. The solvent forming the continuous phase may be immiscible to the catalyst solution at least at the conditions (e.g. temperatures) used during the dispersing step.

The term "immiscible with the catalyst solution" means that the solvent (continuous phase) is fully immiscible or partly immiscible i.e. not fully miscible with the dispersed phase solution.

Preferably said solvent is inert in relation to the compounds of the catalyst system to be produced. Full disclosure of the necessary process can be found in WO03/051934 which is herein incorporated by reference.

The inert solvent must be chemically inert at least at the conditions (e.g. temperature) used during the dispersing step. Preferably, the solvent of said continuous phase does not contain dissolved therein any significant amounts of catalyst forming compounds. Thus, the solid particles of the catalyst are formed in the droplets from the compounds which originate from the dispersed phase (i.e. are provided to the emulsion in a solution dispersed into the continuous phase).

The terms "immobilisation" and "solidification" are used herein interchangeably for the same purpose, i.e. for forming free flowing solid catalyst particles in the absence of an external porous particulate carrier, such as silica. The solidification happens thus within the droplets. Said step can be effected in various ways as disclosed in said WO03/051934 Preferably solidification is caused by an external stimulus to the emulsion system such as a temperature change to cause the solidification. Thus in said step the catalyst component (s) remain "fixed" within the formed solid particles. It is also possible that one or more of the catalyst components may take part in the solidification/immobilisation reaction.

Accordingly, solid, compositionally uniform particles having a predetermined particle size range can be obtained.

Furthermore, the particle size of the catalyst particles of the invention can be controlled by the size of the droplets in the solution, and spherical particles with a uniform particle size distribution can be obtained.

The invention is also industrially advantageous, since it enables the preparation of the solid particles to be carried out as a one-pot procedure. Continuous or semicontinuous processes are also possible for producing the catalyst.

Dispersed Phase

The principles for preparing two phase emulsion systems are known in the chemical field. Thus, in order to form the two phase liquid system, the solution of the catalyst component (s) and the solvent used as the continuous liquid phase have to be essentially immiscible at least during the dispersing step. This can be achieved in a known manner e.g. by choosing said two liquids and/or the temperature of the dispersing step/solidifying step accordingly.

A solvent may be employed to form the solution of the catalyst component (s). Said solvent is chosen so that it dissolves said catalyst component (s). The solvent can be preferably an organic solvent such as used in the field, comprising an optionally substituted hydrocarbon such as linear or branched aliphatic, alicyclic or aromatic hydrocarbon, such as a linear or cyclic alkane, an aromatic hydrocarbon and/or a halogen containing hydrocarbon.

Examples of aromatic hydrocarbons are toluene, benzene, ethylbenzene, propylbenzene, butylbenzene and xylene. Toluene is a preferred solvent. The solution may comprise one or more solvents. Such a solvent can thus be used to facilitate the emulsion formation, and usually does not form part of the solidified particles, but e.g. is removed after the solidification step together with the continuous phase.

Alternatively, a solvent may take part in the solidification, e.g. an inert hydrocarbon having a high melting point (waxes), such as above 40° C., suitably above 70° C., e.g. above 80° C. or 90° C., may be used as solvents of the dispersed phase to immobilise the catalyst compounds within the formed droplets.

In another embodiment, the solvent consists partly or completely of a liquid monomer, e.g. liquid olefin monomer designed to be polymerised in a "prepolymerisation" immobilisation step.

Continuous Phase

The solvent used to form the continuous liquid phase is a single solvent or a mixture of different solvents and may be immiscible with the solution of the catalyst components at least at the conditions (e.g. temperatures) used during the dispersing step. Preferably said solvent is inert in relation to said compounds.

The term "inert in relation to said compounds" means herein that the solvent of the continuous phase is chemically inert, i.e. undergoes no chemical reaction with any catalyst forming component. Thus, the solid particles of the catalyst are formed in the droplets from the compounds which originate from the dispersed phase, i.e. are provided to the emulsion in a solution dispersed into the continuous phase.

It is preferred that the catalyst components used for forming the solid catalyst will not be soluble in the solvent of the continuous liquid phase. Preferably, said catalyst components are essentially insoluble in said continuous phase forming solvent.

Solidification takes place essentially after the droplets are formed, i.e. the solidification is effected within the droplets e.g. by causing a solidifying reaction among the compounds present in the droplets. Furthermore, even if some solidifying agent is added to the system separately, it reacts within the droplet phase and no catalyst forming components go into the continuous phase.

The term "emulsion" used herein covers both bi- and multiphasic systems.

In a preferred embodiment said solvent forming the continuous phase is an inert solvent including a halogenated organic solvent or mixtures thereof, preferably fluorinated organic solvents and particularly semi, highly or perfluorinated organic solvents and functionalised derivatives thereof. Examples of the above-mentioned solvents are semi, highly or perfluorinated hydrocarbons, such as alkanes, alkenes and cycloalkanes, ethers, e.g. perfluorinated ethers and amines, particularly tertiary amines, and functionalised derivatives thereof. Preferred are semi, highly or perfluorinated, particularly perfluorinated hydrocarbons, e.g. perfluorohydrocarbons of e.g. C3-C30, such as C4-C10. Specific examples of suitable perfluoroalkanes and perfluorocycloalkanes include perfluoro-hexane, -heptane, -octane and -(methylcyclohexane). Semi fluorinated hydrocarbons relates particularly to semifluorinated n-alkanes, such as perfluoroalkyl-alkane.

"Semi fluorinated" hydrocarbons also include such hydrocarbons wherein blocks of —C—F and —C—H alternate. "Highly fluorinated" means that the majority of the —C—H units are replaced with —C—F units. "Perfluorinated" means that all —C—H units are replaced with —C—F units. See the articles of A. Enders and G. Maas in "Chemie in unserer Zeit", 34. Jahrg. 2000, Nr.6, and of Pierandrea Lo Nostro in "Advances in Colloid and Interface Science", 56 (1995) 245-287, Elsevier Science.

Dispersing Step

The emulsion can be formed by any means known in the art: by mixing, such as by stirring said solution vigorously to said solvent forming the continuous phase or by means of mixing mills, or by means of ultra sonic wave, or by using a so called phase change method for preparing the emulsion by first forming a homogeneous system which is then transferred by changing the temperature of the system to a biphasic system so that droplets will be formed.

The two phase state is maintained during the emulsion formation step and the solidification step, as, for example, by appropriate stirring.

Additionally, emulsifying agents/emulsion stabilisers can be used, preferably in a manner known in the art, for facilitating the formation and/or stability of the emulsion. For the said purposes e.g. surfactants, e.g. a class based on hydrocarbons (including polymeric hydrocarbons with a molecular weight e.g. up to 10 000 and optionally interrupted with a heteroatom(s)), preferably halogenated hydrocarbons, such as semi- or highly fluorinated hydrocarbons optionally having a functional group selected e.g. from —OH, —SH, $NH_2$, $NR"_2$, —COOH, —$COONH_2$, oxides of alkenes, —CR"=$CH_2$, where R" is hydrogen, or C1-C20 alkyl, C2-20-alkenyl or C2-20-alkynyl group, oxo-groups, cyclic ethers and/or any reactive derivative of these groups, like alkoxy, or carboxylic acid alkyl ester groups, or, preferably semi-, highly- or perfluorinated hydrocarbons having a functionalised terminal, can be used. The surfactants can be added to the catalyst solution, which forms the dispersed phase of the emulsion, to facilitate the forming of the emulsion and to stabilize the emulsion.

Alternatively, an emulsifying and/or emulsion stabilising aid can also be formed by reacting a surfactant precursor bearing at least one functional group with a compound reactive with said functional group and present in the catalyst solution or in the solvent forming the continuous phase. The obtained reaction product acts as the actual emulsifying aid and or stabiliser in the formed emulsion system.

Examples of the surfactant precursors usable for forming said reaction product include e.g. known surfactants which bear at least one functional group selected e.g. from —OH, —SH, $NH_2$, $NR"_2$, —COOH, —$COONH_2$, oxides of alkenes, —CR"=$CH_2$, where R" is hydrogen, or C1-C20 alkyl, C2-20-alkenyl or C2-20-alkynyl group, oxo-groups, cyclic ethers with 3 to 5 ring atoms, and/or any reactive derivative of these groups, like alkoxy or carboxylic acid alkyl ester groups; e.g. semi-, highly or perfluorinated hydrocarbons bearing one or more of said functional groups. Preferably, the surfactant precursor has a terminal functionality as defined above.

The compound reacting with such surfactant precursor is preferably contained in the catalyst solution and may be a further additive or one or more of the catalyst forming compounds. Such compound is e.g. a compound of group 13 (e.g. MAO and/or an aluminium alkyl compound and/or a transition metal compound).

If a surfactant precursor is used, it is preferably first reacted with a compound of the catalyst solution before the addition of the transition metal compound. In one embodiment e.g. a highly fluorinated C1-n (suitably C4-30- or C5-15) alcohol (e.g. highly fluorinated heptanol, octanol or nonanol), oxide (e.g. propenoxide) or acrylate ester is reacted with a cocatalyst to form the "actual" surfactant. Then, an additional amount of cocatalyst and the transition metal compound is added to said solution and the obtained solution is dispersed to the solvent forming the continuous phase. The "actual" surfactant solution may be prepared before the dispersing step or in the dispersed system. If said solution is made before the dispersing step, then the prepared "actual" surfactant solution and the transition metal solution may be dispersed successively (e.g. the surfactant solution first) to the immiscible solvent, or be combined together before the dispersing step.

Solidification

The solidification of the catalyst component(s) in the dispersed droplets can be effected in various ways, e.g. by causing or accelerating the formation of said solid catalyst forming reaction products of the compounds present in the droplets. This can be effected, depending on the used compounds and/or the desired solidification rate, with or without an external stimulus, such as a temperature change of the system.

In a particularly preferred embodiment, the solidification is effected after the emulsion system is formed by subjecting the system to an external stimulus, such as a temperature change. Temperature differences of e.g. 5 to 100° C., such as 10 to 100° C., or 20 to 90° C., such as 50 to 90° C.

The emulsion system may be subjected to a rapid temperature change to cause a fast solidification in the dispersed system. The dispersed phase may e.g. be subjected to an immediate (within milliseconds to few seconds) temperature change in order to achieve an instant solidification of the component (s) within the droplets. The appropriate temperature change, i.e. an increase or a decrease in the temperature of an emulsion system, required for the desired solidification rate of the components cannot be limited to any specific range, but naturally depends on the emulsion system, i. a. on the used compounds and the concentrations/ratios thereof, as well as on the used solvents, and is chosen accordingly. It is also evident that any techniques may be used to provide sufficient heating or cooling effect to the dispersed system to cause the desired solidification.

In one embodiment the heating or cooling effect is obtained by bringing the emulsion system with a certain temperature to an inert receiving medium with significantly different temperature, e.g. as stated above, whereby said temperature change of the emulsion system is sufficient to cause the rapid solidification of the droplets. The receiving medium can be gaseous, e.g. air, or a liquid, preferably a solvent, or a mixture of two or more solvents, wherein the catalyst component (s) is (are) immiscible and which is inert in relation to the catalyst component (s). For instance, the receiving medium comprises the same immiscible solvent used as the continuous phase in the first emulsion formation step.

Said solvents can be used alone or as a mixture with other solvents, such as aliphatic or aromatic hydrocarbons, such as alkanes. Preferably a fluorinated solvent as the receiving medium is used, which may be the same as the continuous phase in the emulsion formation, e.g. perfluorinated hydrocarbon.

Alternatively, the temperature difference may be effected by gradual heating of the emulsion system, e.g. up to 10° C. per minute, preferably 0.5 to 6° C. per minute and more preferably in 1 to 5° C. per minute.

In case a melt of e.g. a hydrocarbon solvent is used for forming the dispersed phase, the solidification of the droplets may be effected by cooling the system using the temperature difference stated above.

Preferably, the "one phase" change as usable for forming an emulsion can also be utilised for solidifying the catalytically active contents within the droplets of an emulsion system by, again, effecting a temperature change in the dispersed system, whereby the solvent used in the droplets becomes miscible with the continuous phase, preferably a fluorous continuous phase as defined above, so that the droplets become impoverished of the solvent and the solidifying components remaining in the "droplets" start to solidify. Thus the immiscibility can be adjusted with respect to the solvents and conditions (temperature) to control the solidification step.

The miscibility of e.g. organic solvents with fluorous solvents can be found from the literature and be chosen accordingly by a skilled person. Also the critical temperatures needed for the phase change are available from the literature or can be determined using methods known in the art, e.g. the Hildebrand-Scatchard-Theorie. Reference is also made to the articles of A. Enders and G. and of Pierandrea Lo Nostro cited above.

Thus according to the invention, the entire or only part of the droplet may be converted to a solid form. The size of the "solidified" droplet may be smaller or greater than that of the original droplet, e.g. if the amount of the monomer used for the prepolymerisation is relatively large.

The solid catalyst particles recovered can be used, after an optional washing step, in a polymerisation process of an olefin. Alternatively, the separated and optionally washed solid particles can be dried to remove any solvent present in the particles before use in the polymerisation step. The separation and optional washing steps can be effected in a known manner, e.g. by filtration and subsequent washing of the solids with a suitable solvent.

The droplet shape of the particles may be substantially maintained. The formed particles may have an average size range of 1 to 500 µm, e.g. 5 to 500 µm, advantageously 5 to 200 µm or 10 to 150 µm. Even an average size range of 5 to 60 µm is possible. The size may be chosen depending on the polymerisation the catalyst is used for. Advantageously, the particles are essentially spherical in shape, they have a low porosity and a low surface area.

The formation of solution can be effected at a temperature of 0-100° C., e.g. at 20-80° C. The dispersion step may be effected at −20° C.-100° C., e.g. at about −10-70° C., such as at −5 to 30° C., e.g. around 0° C.

To the obtained dispersion an emulsifying agent as defined above, may be added to improve/stabilise the droplet formation. The solidification of the catalyst component in the droplets is preferably effected by raising the temperature of the mixture, e.g. from 0° C. temperature up to 100° C., e.g. up to 60-90° C., gradually. E.g. in 1 to 180 minutes, e.g. 1-90 or 5-30 minutes, or as a rapid heat change. Heating time is dependent on the size of the reactor.

During the solidification step, which is preferably carried out at about 60 to 100° C., preferably at about 75 to 95° C., (below the boiling point of the solvents) the solvents may preferably be removed and optionally the solids are washed with a wash solution, which can be any solvent or mixture of solvents such as those defined above and/or used in the art, preferably a hydrocarbon, such as pentane, hexane or heptane, suitably heptane. The washed catalyst can be dried or it can be slurried into an oil and used as a catalyst-oil slurry in polymerisation process.

All or part of the preparation steps can be done in a continuous manner. Reference is made to WO2006/069733 describing principles of such a continuous or semicontinuous preparation methods of the solid catalyst types, prepared via emulsion/solidification method.

Polymerisation

The olefin polymerized using the catalyst of the invention is preferably propylene or a higher alpha-olefin. It may also be ethylene or a mixture of ethylene and an α-olefin. Alternatively, it may also be mixture of alpha olefins, for example $C_{2-20}$ olefins, e.g. ethylene, propylene, 1-butene, 1-hexene, 4-methyl-1-pentene, 1-octene etc. The olefins polymerized in the method of the invention may include any compound which includes unsaturated polymerizable groups. Thus for example unsaturated compounds, such as $C_{6-20}$ olefins (including cyclic and polycyclic olefins (e.g. norbornene)), and polyenes, especially $C_{4-20}$ dienes, may be included in a comonomer mixture with lower olefins, e.g. $C_{2-5}$ α-olefins. Diolefins (i.e. dienes) are suitably used for introducing long chain branching into the resultant polymer. Examples of such dienes include α,ω linear dienes such as 1,5-hexadiene, 1,6-heptadiene, 1,8-nonadiene, 1,9-decadiene, etc.

The catalysts of the present invention are particularly suited for use in the manufacture of polypropylene polymers, either homopolymers or especially copolymers thereof. Most especially, the catalyst are used to manufacture random copolymers of propylene, e.g. random copolymers of propylene and ethylene.

As comonomers to propylene are preferably used ethylene, or higher olefins, e.g. C4-C12 olefins, like 1-butene, 1-hexene, 1-octene or any mixtures thereof, preferably ethylene. It is especially preferred if the polymer is a propylene ethylene random copolymer. The ethylene content in such a polymer may be up to 7 wt %, e.g. 0.5 to 5 wt %.

Polymerization in the method of the invention may be effected in one or more, e.g. 1, 2 or 3, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase reactors.

In case of propylene polymerisation for slurry reactors, the reaction temperature will generally be in the range 60 to 110° C. (e.g. 60-90° C.), the reactor pressure will generally be in the range 5 to 80 bar (e.g. 20-60 bar), and the residence time will generally be in the range 0.1 to 5 hours (e.g. 0.3 to 2 hours). The monomer is usually used as reaction medium.

For gas phase reactors, the reaction temperature used will generally be in the range 60 to 115° C. (e.g. 70 to 110° C.), the reactor pressure will generally be in the range 10 to 25 bar, and the residence time will generally be 0.5 to 8 hours (e.g. 0.5 to 4 hours). The gas used will be the monomer optionally as mixture with a non-reactive gas such as nitrogen or propane. In addition to actual polymerisation steps and reactors, the process can contain any additional polymerisation steps, like prepolymerisation step, and any further after reactor handling steps as known in the art.

Generally the quantity of catalyst used will depend upon the nature of the catalyst, the reactor types and conditions and the properties desired for the polymer product. As is well known in the art hydrogen can be used for controlling the molecular weight of the polymer. It is particularly notable that the catalyst of the present invention performs exceptionally well over a wide range of hydrogen concentration used during the polymerisation process, which makes the catalyst beneficial to be used for productions of a wide range of polymers This forms a further aspect of the invention. The catalysts are useful at higher hydrogen concentrations as well with lower hydrogen concentrations to get polymer with higher molecular weight. The activity of the catalysts of the invention is also very high as well as the catalyst productivity.

The catalysts of the invention enable the formation of high molecular weight, low xylene soluble polymers which also possess high isotacticity. Preferably, xylene soluble content of the polymer made by the catalyst of the invention is less than 1 wt %, more preferably 0.7 wt % or less and even more preferably less than 0.5 wt %. This is achieved even when ethylene content is in the range of 1 to 5 wt %. Ideally the ethylene content, if a copolymer is prepared, should be 5 wt % or less, e.g. 0.5 to 5 wt %. Ethylene should be the only comonomer present. The molecular weight of the polypropylene copolymers can be at least 300,000, preferably at least 400,000, or even at least 500,000 or even as high as at least 600,000. MFR$_{21}$ values may be less than 30 g/10 min. Being metallocene catalysts, Mw/Mn values are low, e.g. 4 or less, preferably 3 or less.

Melt temperatures of propylene homopolymers produced by the catalyst of the invention may be low, e.g. 147° C. or below, preferably below 147° C. Ideally they will still have low xylene solubles amount (XS), measured as defined in the experimental part. XS is preferably 0.7% or less, preferably 0.5% or less or even 0.4 or 0.3% or less. As example the melt temperature of homopolymers can be in the range of 140-147° C.

The polymers made by the catalysts of the invention are useful in all kinds of end articles such as pipes, films (cast, blown or BOPP films), fibers, moulded articles (e.g. injection moulded, blow moulded, rotomoulded articles), extrusion coatings and so on.

The invention will now be illustrated by reference to the following non-limiting Examples.

Measurement Methods:

Al and Zr Determination (ICP-Method)

The elementary analysis of a catalyst was performed by taking a solid sample of mass, M, cooling over dry ice. Samples were diluted up to a known volume, V, by dissolving in nitric acid (HNO$_3$, 65%, 5% of V) and freshly deionised (DI) water (5% of V). The solution was then added to hydrofluoric acid (HF, 40%, 3% of V), diluted with DI water up to the final volume, V, and left to stabilise for two hours. The analysis was run at room temperature using a Thermo Elemental IRIS Advantage XUV Inductively Coupled Plasma—Atomic Excitation Spectrometer (ICP-AES) which was calibrated immediately before analysis using a blank (a solution of 5% HNO$_3$, 3% HF in DI water), a low standard (10 ppm Al in a solution of 5% HNO$_3$, 3% HF in DI water), a high standard (50 ppm Al, 20 ppm Zr in a solution of 5% HNO$_3$, 3% HF in DI water) and a quality control sample (20 ppm Al, 10 ppm Zr in a solution of 5% HNO$_3$, 3% HF in DI water). The content of zirconium was monitored using the 339.198 nm line, the content of aluminium via the 396.152 nm line and the potassium using the 766.490 nm line. The reported values, required to be between 0 and 100, or further dilution is required, are an average of three successive aliquots taken from the same sample and are related back to the original catalyst using equation 1.

$$C = \frac{R \times V}{M} \qquad \text{Equation 1}$$

Where:
C is the concentration in ppm, related to % content by a factor of 10,000
R is the reported value from the ICP-AES
V is the total volume of dilution in ml
M is the original mass of sample in g
If dilution was required then this also needs to be taken into account by multiplication of C by the dilution factor.

Melting Temperature $T_m$ [° C.] and Crystallisation Temperature $T_c$ [° C.]:

Melting temperature ($T_m$), crystallization temperature ($T_c$), were measured (according to ISO 11357-3:1999) with Mettler TA820 differential scanning calorimetry (DSC) on 5 to 10 mg, typically 8±0.5 mg samples. Both crystallization and melting curves were obtained during 10° C./min cooling and heating scans between 30° C. and 225° C. Melting and crystallization temperatures were taken as the peaks of endotherms and exotherms. The peak temperature of the second heating scan was taken as the melting temperature.

Melt Flow Rate

The melt flow rate (MFR) is determined according to ISO 1133 and is indicated in g/10 min. The MFR is an indication of the flowability, and hence the processability, of the polymer. The higher the melt flow rate, the lower the viscosity of the polymer. The MFR is determined at 230° C. and may be determined at different loadings such as 2.16 kg (MFR$_2$) or 21.6 kg (MFR$_{21}$).

GPC: Molecular Weight Averages, Molecular Weight Distribution, and Polydispersity Index (Mn, Mw, MWD)

Molecular weight averages (Mw, Mn), Molecular weight distribution (MWD) and its broadness, described by polydispersity index, PDI=Mw/Mn (wherein Mn is the number average molecular weight and Mw is the weight average molecular weight) were determined by Gel Permeation Chromatography (GPC) according to ISO 16014-4:2003 and ASTM D 6474-99. A Waters GPCV2000 instrument, equipped with differential refractive index detector and online viscosimeter was used with 2×GMHXL-HT and 1×G7000HXL-HT TSK-gel columns from Tosoh Bioscience and 1,2,4-trichlorobenzene (TCB, stabilized with 250 mg/L 2,6-Di tert butyl-4-methyl-phenol) as solvent at 140° C. and at a constant flow rate of 1 mL/min. 209.5 μL of sample solution were injected per analysis. The column set was calibrated using universal calibration (according to ISO 16014-2:2003) with at least 15 narrow MWD polystyrene (PS) standards in the range of 1 kg/mol to 12 000 kg/mol. Mark Houwink constants for PS, PE and PP used are as per ASTM D 6474-99. All samples were prepared by dissolving 0.5-4.0 mg of polymer in 4 mL (at 140° C.) of stabilized TCB (same as mobile phase) and keeping for max. 3 hours at max. 160° C. with continuous gentle shaking prior sampling into the GPC instrument.

Xylene Solubles 2.0 g of polymer is dissolved in 250 ml p-xylene at 135° C. under agitation. After 30 minutes the solution is allowed to cool for 15 minutes at ambient temperature and then allowed to settle for 30 minutes at 25° C. The solution is filtered with filter paper into two 100 ml flasks. The solution from the first 100 ml vessel is evaporated in nitrogen flow and the residue is dried under vacuum at 90° C. until constant weight is reached.

$XS \% = (100 \cdot m \cdot V_0)/(m_0 \cdot v)$;

$m_0$=initial polymer amount (g); m=weight of residue (g); $V_0$=initial volume (ml); v=volume of analysed sample (ml).

Catalyst Activity

The catalyst activity was calculated on the basis of following formula:

$$\text{Catalyst Activity (kg/g} * \text{h)} = \frac{\text{amount of polymer produced (kg)}}{\text{catalyst loading (g)} \times \text{polymerisation time (h)}}$$

Comonomer Content by $^{13}$C NMR

Quantification of Microstructure by NMR Spectroscopy

Quantitative nuclear-magnetic resonance (NMR) spectroscopy was used to quantify the comonomer content of the polymers.

Quantitative $^{13}$C{$^1$H} NMR spectra were recorded in the solution-state using a Bruker Advance III 400 NMR spectrometer operating at 400.15 and 100.62 MHz for $^1$H and $^{13}$C respectively. All spectra were recorded using a $^{13}$C optimised 10 mm extended temperature probehead at 125° C. using nitrogen gas for all pneumatics. Approximately 200 mg of material was dissolved in 3 ml of 1,2-tetrachloroethane-d$_2$ (TCE-d$_2$) along with chromium-(III)-acetylacetonate (Cr(acac)$_3$) resulting in a 65 mM solution of relaxation agent in solvent as described in G. Singh, A. Kothari, V. Gupta, Polymer Testing 2009, 28(5), 475.

To ensure a homogenous solution, after initial sample preparation in a heat block, the NMR tube was further heated in a rotatory oven for at least 1 hour. Upon insertion into the magnet the tube was spun at 10 Hz. This setup was chosen primarily for the high resolution and quantitatively needed for accurate ethylene content quantification. Standard single-pulse excitation was employed without NOE, using an optimised tip angle, 1 s recycle delay and a bi-level WALTZ16 decoupling scheme as described in Z. Zhou, R. Kuemmerle, X. Qiu, D. Redwine, R. Cong, A. Taha, D. Baugh, B. Winniford, J. Mag. Reson. 187 (2007) 225 and V. Busico, P. Carbonniere, R. Cipullo, C. Pellecchia, J. Severn, G. Talarico, Macromol. Rapid Commun. 2007, 28, 1128. A total of 6144 (6k) transients were acquired per spectra. Quantitative $^{13}$C{$^1$H} NMR spectra were processed, integrated and relevant quantitative properties determined from the integrals. All chemical shifts were indirectly referenced to the central methylene group of the ethylene block (EEE) at 30.00 ppm using the chemical shift of the solvent. This approach allowed comparable referencing even when this structural unit was not present.

With characteristic signals corresponding to 2.1 erythro regio defects observed (as described in L. Resconi, L. Cavallo, A. Fait, F. Piemontesi, Chem. Rev. 2000, 100 (4), 1253, in Cheng, H. N., Macromolecules 1984, 17, 1950, and in W-J. Wang and S. Zhu, Macromolecules 2000, 33 1157) the correction for the influence of the regio defects on determined properties was required. Characteristic signals corresponding to other types of regio defects were not observed.

Characteristic signals corresponding to the incorporation of ethylene were observed (as described in Cheng, H. N., Macromolecules 1984, 17, 1950) and the comonomer fraction calculated as the fraction of ethylene in the polymer with respect to all monomer in the polymer:

$fE=(E/(P+E)$

The comonomer fraction was quantified using the method of W-J. Wang and S. Zhu, Macromolecules 2000, 33 1157, through integration of multiple signals across the whole spectral region in the $^{13}$C{$^1$H} spectra. This method was chosen for its robust nature and ability to account for the presence of regio-defects when needed. Integral regions were slightly adjusted to increase applicability across the whole range of encountered comonomer contents.

The mole percent comonomer incorporation was calculated from the mole fraction:

$E \text{ [mol \%]} = 100 * fE$

The weight percent comonomer incorporation was calculated from the mole fraction:

$E \text{ [wt \%]} = 100 * (fE*28.06)/((fE*28.06)+((1-fE)*42.08))$ $^{13}$C NMR—Regio Errors Measurement Quantitative solution state $^{13}$C{$^1$H} nuclear magnetic resonance (NMR) spectra were recorded using a Bruker Avance III 400 NMR spectrometer with a 9.4 T superconducting standard-bore magnet operating at 400.15 and 100.62 MHz for $^1$H and $^{13}$C respectively. Approximately 200 mg of material were dissolved in approximately 3 ml of 1,1,2,2-tetrachloroethane-d$_2$ (TCE-d$_2$) inside a 10 mm NMR tube. The measurements were done at 125° C. using a $^{13}$C optimised 10 mm selective excitation probehead with nitrogen gas for all pneumatics. The data were acquired with standard 90° single-pulse excitation with NOE and bi-level WALTZ16 decoupling scheme. A total of 6144 transients were acquired per spectra using a cycle delay of 3 seconds and an acquisition time of 1.6 second.

The tacticity distribution at the triad level and regioerrors were determined from the quantitative $^{13}$C{$^{1}$H} NMR spectra after basic assignment as in: V. Busico and R. Cipullo, Progress in Polymer Science, 2001, 26, 443-533, and based on the method described in: C. De Rosa, F. Auriemma, M. Paolillo, L. Resconi, I. Camurati, Macromolecules 2005, 38(22), 9143-9154.

Quantification of the pentad distribution was done through integration of the methyl region in the $^{13}$C{$^{1}$H} spectra and when applicable corrected for any sites not related to the stereo sequences of interest, e.g. regio misinsertions.

EXAMPLES

General Procedures and Starting Materials

All manipulations with air and moisture sensitive compounds were performed either in an atmosphere of thoroughly purified argon using a standard Schlenk technique or in a controlled atmosphere Glove Box (Mecaplex, VAC or M. Braun).

tert-Butyl-2-methoxybenzene was obtained from 2-tert-butylphenol (Merck) and dimethylsulfate (Merck) in the presence of 40% NaOH (Reachim) and $^n$Bu$_4$NBr (Acros) in dichloromethane as described in [. WO 2007116034, 2007 for Basell Polyolefine GmbH]. Diethyl malonate (Acros), isobutylbromide (Acros), pivaldehyde (Acros), diethylamine (Acros), paraform (Acros), methanesulfonic acid (Aldrich), Et$_4$NI (Acros), Pd(OAc)$_2$ (Aldrich), NaBPh$_4$ (Aldrich), di-tert-butyl(2'-methyl-2-biphenyl)phosphine (Aldrich), TsOH (Acros), 2.5 M $^n$BuLi in hexanes (Chemetall), NaBH$_4$ (Aldrich), CuCN (Merck), ZrCl$_4$(THF)$_2$ (Aldrich), silica gel 60 (40-63 um, Merck), bromine (Merck), KOH (Merck), Na$_2$SO$_4$ (Akzo Nobel), 12 M HCl (Reachim, Russia), methanol (Merck), CDCl$_3$ (Deutero GmbH), CH$_2$Cl$_2$ (Merck), 96% ethanol (Merck), anhydrous ethanol (Merck), methanol (Merck), potassium acetate (Acros), Na$_2$SO$_3$ (Merck), Na$_2$CO$_3$ (Merck), K$_2$CO$_3$ (Merck), ZnCl$_2$ (Merck), P$_4$O$_{10}$ (Merck), sodium lump (Merck), hydrogen gas (Linde), acetic anhydride (Acros), tetrahydrofurane (Merck), hexanes (Merck), toluene (Merck), ethyl acetate (Merck), diethyl ether (Merck) for extractions and dichloromethane (Merck) were used as received. Tetrahydrofurane (Merck) and diethyl ether (Merck) freshly distilled from benzophenone ketyl were used for organometallic synthesis and catalysis. DMF (Merck) was dried and distilled over CaH$_2$. CD$_2$Cl$_2$ (Deutero GmbH) for NMR experiments was dried and kept over CaH$_2$. Toluene (Merck) and hexanes (Merck) for organometallic synthesis were kept and distilled over Na/K alloy.

MAO was purchased from Albermarle and used as a 30 wt-% solution in toluene. Perfluoroalkylethyl acrylate esters (CAS number 65605-70-1) was purchased from the Cytonix corporation, dried over activated molecular sieves (2 times) and degassed by argon bubbling prior to use. Hexadecafluoro-1,3-dimethylcyclohexane (PFC), dried over activated molecular sieves (2 times) and degassed by argon bubbling prior to use. Propylene is provided by Borealis and adequately purified before use. Triethylaluminum was purchased from Crompton and used in pure form. Hydrogen is provided by AGA and purified before use.

Example 1

Manufacture of rac-Dimethylsilylene-bis(6-tert-butyl-2-isobutyl-5-methoxy-4-phenyl-1H-inden-1-yl) zirconium dichloride

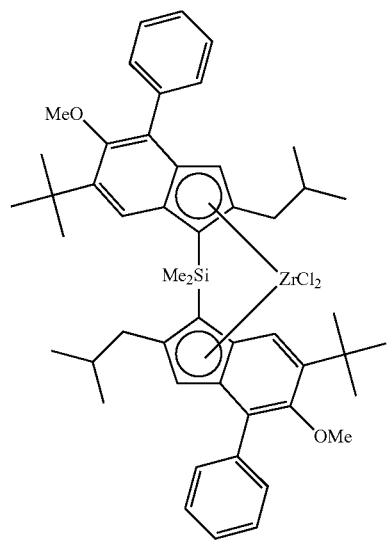

Isobutylmalonic acid

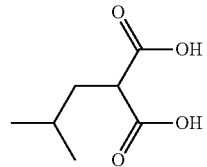

To a solution of sodium ethoxide obtained from 46.0 g (2.00 mol) of sodium lump and 1000 cm$^3$ of anhydrous ethanol 320 g (2.00 mol) of diethyl malonate was added at room temperature. The obtained mixture was stirred for 30 min at this temperature, and then 274 g (2.00 mol) of isobutylbromide was added. The resulting mixture was refluxed for 5 h, and then ethanol was distilled off. To the cooled residue 1500 ml of cold water and 500 ml of ethyl acetate were added. The organic layer was separated, dried over Na$_2$SO$_4$ and then evaporated to dryness. Fractional rectification of the residue gave 357 g of colorless liquid, bp 177-187° C./220 mm Hg. This product contained ca. 10% of diethyl malonate. To a solution of 117.3 g (542 mmol) of diethyl isobutylmalonate in 500 ml of methanol a solution of 125 g of potassium hydroxide in 1000 cm$^3$ of water was added. The resulting mixture was refluxed for 5 h, then ethanol and methanol were distilled off. Further on, 1000 cm$^3$ of water was added, and then this mixture was acidified by 12 M HCl to pH 1.0. Isobutylmalonic acid was extracted by 4×500 ml of ether. The combined extract was evaporated to dryness. To the residue 300 ml of toluene was added. Again, the obtained mixture was evaporated to dryness to remove moisture. To a solution of the residue in 150 ml of toluene 500 ml of hexanes was added.

The formed precipitate was filtered off, washed by 50 ml of hexanes and dried in vacuum. This procedure gave 72.8 g (84%) of the title product as white crystalline solid.

Anal. calc. for $C_7H_{12}O_4$: C, 52.49; H, 7.55. Found: C, 52.18; H, 7.71.

$^1$H NMR (CDCl$_3$): δ 11.75 (br.s, 2H, CO$_2$H), 3.52 (t, J=7.6 Hz, 1H, CHCO$_2$H), 1.83 (dt, J=7.6 Hz, J=6.6 Hz, 2H, CH$_2$), 1.65 (d-sept, J=7.6 Hz, J=6.6 Hz, 1H, Me$_2$CH), 0.94 (d, J=6.6 Hz, 6H, Me$_2$CH). $^{13}$C NMR (CDCl$_3$): δ 175.5, 49.9, 37.4, 28.1, 22.1.

2-Isobutylacrylic acid

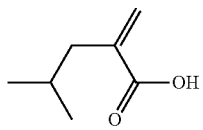

To a solution of 72.9 g (0.455 mol) of isobutylmalonic acid in 650 ml of ethyl acetate 54.2 ml (38.3 g, 0.524 mol) of diethylamine was added dropwise at 5° C. To the obtained suspension 19.2 g (0.640 mol) of paraform was added. The resulting mixture was refluxed for 5 h, then cooled to 5° C., and 350 ml of ether and 1000 cm$^3$ of 2M HCl were added. After mixing the organic layer was separated, the aqueous layer was additionally extracted with 2×500 ml of ether. The combined organic extract was dried over Na$_2$SO$_4$ and then evaporated to dryness. Rectification of the residue in vacuum gave the title product, bp 75-77° C./6 mm Hg. Yield 51.5 g (88%) of colorless liquid.

Anal. calc. for $C_7H_{12}O_2$: C, 65.60; H, 9.44. Found: C, 65.78; H, 9.53.

$^1$H NMR (CDCl$_3$): δ 12.0 (br.s, 1H, CO$_2$H), 6.31 (d, J=1.5 Hz, 1H, CHH'=C), 5.60 (m, 1H, CHH'=C), 2.17 (dd, J=7.1 Hz, J=0.9 Hz, 2H, $^i$PrCH$_2$), 1.82 (nonet, J=6.7 Hz, 1H, CHMe$_2$), 1.82 (d, J=6.7 Hz, 6H, CHMe$_2$). $^{13}$C NMR (CDCl$_3$): δ 173.3, 139.2, 128.2, 40.9, 27.1, 22.2.

6-tert-Butyl-2-isobutyl-5-methoxyindan-1-one

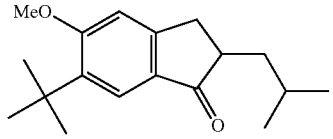 [SMILES: COc1cc2c(cc1C(C)(C)C)C(=O)C(CC(C)C)C2]

To Iton reagent (obtained from 110 g of P$_4$O$_{10}$ and 560 ml of methanesulfonic acid at 110° C.) a mixture of 59.4 g (0.362 mol) of 1-tert-butyl-2-methoxybenzene and 51.5 g (0.402 mol) of 2-isobutylacrylic acid was added dropwise at vigorous stirring in such a rate to maintain temperature at 60±1° C. (for ca. 40 min). The resulting mixture was stirred for 40 min at 65° C., cooled to room temperature, and then poured on 1000 cm$^3$ of ice with 1000 cm$^3$ of water. The product was extracted by 3×500 ml of dichloromethane. The combined organic extract was washed by aqueous K$_2$CO$_3$, dried over Na$_2$SO$_4$ and then evaporated to dryness. Fractional rectification of the residue gave dark red oil, b.p. 165-174° C./5 mm Hg. This oil was recrystallized from 100 ml of hexanes. White crystals precipitated at 5° C. were collected, washed by 20 ml of cold hexanes, and dried in vacuum. Yield 24.9 g (25%) of the title product.

Anal. calc. for $C_{18}H_{26}O_2$: C, 78.79; H, 9.55. Found: C, 78.65; H, 9.42.

$^1$H NMR (CDCl$_3$): δ 7.66 (s, 1H, 7-H in indanone), 6.85 (s, 1H, 4-H in indanone), 3.91 (s, 3H, OMe), 3.22 (dd, J=17.0 Hz, J=7.5 Hz, 1H, 3-H in indanone), 2.70 (dd, J=17.0 Hz, J=3.7 Hz, 1H, 3'-H in indanone), 2.65 (m, 1H, 2-H in indanone), 1.80 (m, 2H, CHH'CHMe$_2$ and CHMe$_2$), 1.36 (s, 9H, $^t$Bu), 1.25 (m, 1H, CHH'CHMe$_2$), 0.96 (d, J=6.3 Hz, 6H, CHMe$_2$). $^{13}$C NMR (CDCl$_3$): δ 208.0, 164.6, 154.6, 138.8, 129.2, 122.0, 107.8, 55.2, 46.1, 41.0, 35.1, 33.1, 29.6, 26.7, 23.5, 21.7.

4-Bromo-6-tert-butyl-2-isobutyl-5-methoxyindan-1-one

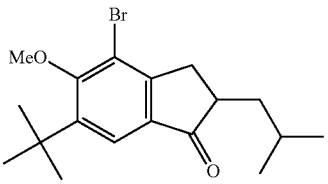 [SMILES: COc1c(C(C)(C)C)cc2c(c1Br)CC(CC(C)C)C2=O]

To a mixture of 24.9 g (90.9 mmol) of 6-tert-butyl-2-isobutyl-5-methoxyindan-1-one, 25.8 g of potassium acetate, 0.5 g of Et$_4$NI, 50 ml of dichloromethane and 150 ml of water 4.66 ml (14.5 g, 90.9 mmol) of bromine was added dropwise by vigorous stirring at 5° C. for 5 min. This mixture was stirred at 5° C. for 3 h, then 15.2 g of potassium acetate was added, and finally 2.56 ml (8.24 g, 51.6 mmol) of bromine was added. The resulting mixture was additionally stirred at this temperature for 1 h. and then washed by aqueous Na$_2$SO$_3$ to remove an excess of bromine. The product was extracted by 3×150 ml of dichloromethane, The combined organic extract was dried over K$_2$CO$_3$, evaporated to dryness, and the residue was dried in vacuum. This procedure gave 31.9 g (99%) of yellowish crystalline material which was further used without an additional purification.

Anal. calc. for $C_{18}H_{25}BrO_2$: C, 61.19; H, 7.13. Found: C, 60.98; H, 6.99.

$^1$H NMR (CDCl$_3$): δ 7.66 (s, 1H, 7-H in indanone), 3.99 (s, 3H, OMe), 3.20 (dd, J=17.1 Hz, J=7.4 Hz, 1H, 3-H in indanone), 2.68 (m, 1H, 2-H in indanone), 2.62 (dd, J=17.1 Hz, J=3.8 Hz, 1H, 3'-H in indanone), 1.80 (m, 2H, CHH'CHMe$_2$ and CHMe$_2$), 1.37 (s, 9H, $^t$Bu), 1.27 (m, 1H, CHH'CHMe$_2$), 0.96 (d, J=6.3 Hz, 6H, CHMe$_2$). $^{13}$C NMR (CDCl$_3$): δ 207.8, 162.7, 154.1, 145.4, 133.0, 121.4, 116.6, 61.6, 46.1, 40.7, 35.6, 34.5, 30.6, 26.5, 23.6, 21.6.

6-tert-Butyl-2-isobutyl-5-methoxy-4-phenylindan-1-one

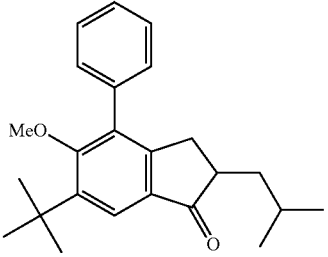 [SMILES: COc1c(C(C)(C)C)cc2c(c1-c1ccccc1)CC(CC(C)C)C2=O]

A mixture of 31.9 g (90.3 mmol) of 4-bromo-6-tert-butyl-2-isobutyl-5-methoxyindan-1-one, 12.7 g (37.1 mmol) of NaBPh$_4$, 0.223 g (0.993 mmol, 1.1 mol. %) of Pd(OAc)$_2$, 0.464 g (1.49 mmol, 1.65 mol. %) of di-tert-butyl(2'-methyl-2-biphenylyl)phosphine, 20.0 g of $Na_2CO_3$, 300 ml of THF and 150 ml of water was refluxed for 10 h. Further on, 500 ml of water was added, and the product was extracted with 3×200 ml of dichloromethane. The combined organic extract was dried over $K_2CO_3$ and then evaporated to dryness. The product was isolated by flash-chromatography on silica gel 60 (40-63 um, eluent: hexanes-dichloromethane=2:1 and then 1:1, vol.). Yield 15.7 g (50%) of yellowish crystalline material.

Anal. calc. for $C_{24}H_{30}O_2$: C, 82.24; H, 8.63. Found: C, 82.38; H, 8.77.

$^1H$ NMR ($CDCl_3$): δ 7.74 (s, 1H, 7-H in indanone), 7.35-7.51 (m, 5H, Ph), 3.27 (s, 3H, OMe), 3.05 (dd, J=17.4 Hz, J=7.6 Hz, 1H, 3-H in indanone), 2.62 (m, 1H, 2-H in indanone), 2.50 (dd, J=17.4 Hz, J=3.3 Hz, 1H, 3'-H in indanone), 1.79 (m, 1H, CHH'CHMe$_2$), 1.70 (m, 1H, CHMe$_2$), 1.41 (s, 9H, $^t$Bu), 1.25 (m, 1H, CHH'CHMe$_2$), 0.96 (d, J=5.5 Hz, 3H, CHMeMe'), 0.96 (d, J=5.5 Hz, 3H, CHMeMe'). $^{13}C$ NMR ($CDCl_3$): δ 208.6, 163.4, 152.8, 143.4, 136.4, 132.5, 131.4, 129.5, 128.7, 127.5, 121.5, 60.5, 46.1, 40.7, 35.4, 32.6, 30.5, 26.4, 23.5, 21.4.

5-tert-Butyl-2-isobutyl-6-methoxy-7-phenyl-1H-indene

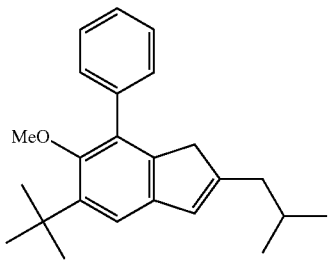 [SMILES: COc1c(C(C)(C)C)cc2c(c1-c1ccccc1)CC(CC(C)C)=C2]

To a solution of 9.0 g (25.7 mmol) of 6-tert-butyl-2-isobutyl-5-methoxy-4-phenylindan-1-one in 100 ml of THF and 50 ml of methanol 10.0 g (0.265 mol) of $NaBH_4$ was added by small portions by vigorous stirring for ca. 1.5 h at room temperature. This mixture was additionally stirred overnight and then acidified by 2 M HCl to pH 1. The product was extracted with 3×150 ml of dichloromethane. The organic extract was evaporated to dryness, and a mixture of the residue with 150 ml of toluene and 0.5 g of TsOH was refluxed for 15 min using Dean-Stark head. The obtained solution was washed by 10% aqueous $K_2CO_3$. The organic layer was separated, and the aqueous layer was extracted with 2×50 ml of dichloromethane. The combined organic extract was dried over $K_2CO_3$, evaporated to dryness, and then passed through short layer of silica gel 60 (40-63 um). The silica gel layer was additionally washed by hexanes-dichloromethane (1:1, vol.). The elute was evaporated to dryness, and the residue was dried in vacuum. This procedure gave 8.52 g (99%) of yellowish oil of the title product which was further used without an additional purification.

Anal. calc. for $C_{24}H_{30}O$: C, 86.18; H, 9.04. Found: C, 86.35; H, 9.12.

$^1H$ NMR ($CDCl_3$): δ 7.48-7.51 (m, 2H, 2,6-H in Ph), 7.41-7.46 (m, 2H, 3,5-H in Ph), 7.32-7.37 (m, 1H, 4-H in Ph), 7.25 (d, J=1.9 Hz, 1H, 4-H in indene), 6.46 (m, 1H, 3-H in indene), 3.22 (s, 3H, OMe), 3.12 (m, 2H, 1,1'-H in indene), 2.26 (d, J=7.1 Hz, 2H, $CH_2CHMe_2$), 1.80 (sept, J=6.8 Hz, 1H, $CHMe_2$), 1.44 (s, 9H, $^t$Bu), 0.89 (d, J=6.6 Hz, 6H, $CHMe_2$).

$^{13}C$ NMR ($CDCl_3$): δ 149.2, 141.6, 141.1, 140.6, 139.4, 138.5, 131.6, 129.6, 128.4, 127.2, 126.9, 117.4, 60.7, 41.3, 40.8, 35.2, 31.0, 28.2, 22.6.

Bis(6-tert-butyl-2-isobutyl-5-methoxy-4-phenyl-1H-inden-1-yl)(dimethyl)silane

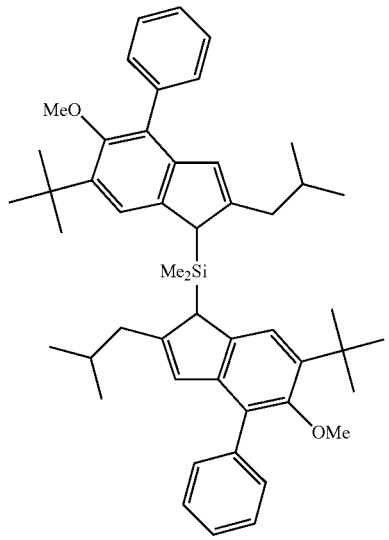

To a solution of 8.50 g (25.4 mmol) of 5-tert-butyl-2-isobutyl-6-methoxy-7-phenyl-1H-indene in 250 ml of ether 10.2 ml (25.5 mmol) of 2.5 M $^n$BuLi in hexanes was added at −50° C. This mixture was stirred for 12 h at room temperature, cooled again to −50° C., and then 0.100 g (1.12 mmol) of CuCN was added. Further on, this mixture was stirred for 15 min at −25° C., cooled to −40° C., and 1.64 g (12.7 mmol) of dichlorodimethylsilane was added in single portion. The resulting mixture was stirred overnight at room temperature, and then 0.5 ml of water and 100 ml of benzene were added. This mixture was filtered through short layer of silica gel 60 (40-63 um). This layer was additionally washed by 100 ml of dichloromethane. The obtained filtrate was evaporated to dryness, and the residue was dried in vacuum. This procedure gave 9.18 g (99%) of yellowish solid which was found to be a ca. 1 to 1 mixture of rac- and meso-compounds.

Anal. calc. for $C_{50}H_{64}O_2Si$: C, 82.82; H, 8.90. Found: C, 83.07; H, 9.10.

$^1H$ NMR ($CDCl_3$): δ 7.42-7.57 (m, 16H, 2,3,5,6-H in Ph of rac- and meso-compounds), 7.33-7.40 (m, 8H, 4-H in Ph and 7-H in indenyl of rac- and meso-compounds), 6.47 (s, 2H, 3-H in indenyl of meso-compound), 6.32 (s, 2H, 3-H in indenyl of rac-compound), 3.69 (s, 2H, 1-H in indenyl of meso-compound), 3.67 (s, 2H, 1-H in indenyl of rac-compound), 3.24 (s, 12H, OMe of rac- and meso-compounds), 2.25-2.43 (m, 6H), 1.83-2.03 (m, 6H), 1.46 (s, 18H, $^t$Bu in rac-compound), 1.44 (s, 18H, $^t$Bu in meso-compound), 0.92 (d, J=6.6 Hz, 6H, CHMeMe' of meso-compound), 0.84 (d, J=6.6 Hz, 6H, CHMeMe' of meso-compound), 0.82 (d, J=6.6 Hz, 6H, CHMeMe' of rac-compound), 0.71 (d, J=6.6 Hz, 6H, CHMeMe' of rac-compound), −0.06 (s, 6H, $Me_2Si$ of rac-compound), −0.14 (s, 3H, MeMe'Si of meso-compound), −0.36 (s, 3H, MeMe'Si of meso-compound). $^{13}C$ NMR ($CDCl_3$): δ 155.4, 155.3, 151.9, 151.2, 143.6, 143.4, 139.5, 139.4, 138.4, 138.3, 137.2, 137.0, 130.30, 130.27, 128.25, 128.22, 127.34, 127.29, 126.60, 126.57, 126.7, 125.3, 120.7, 120.5, 60.52, 60.50, 45.8, 45.7, 41.4, 40.7, 35.20, 35.15, 31.28, 31.24, 28.9, 28.8, 23.30, 23.27, 22.2, 22.0, −4.2, −4.3, −5.1.

Dimethylsilylene-bis(6-tert-butyl-2-isobutyl-5-methoxy-4-phenyl-1H-inden-1-yl)zirconium dichloride

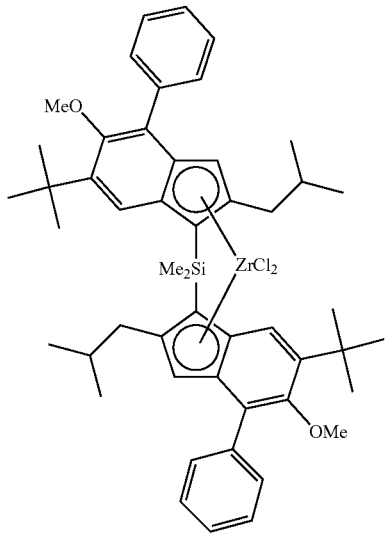

To a solution of 9.18 g (12.7 mmol) of bis(6-tert-butyl-2-isobutyl-5-methoxy-4-phenyl-1H-inden-1-yl)(dimethyl)silane in 200 ml of ether 10.1 ml (25.3 mmol) of 2.5 M "BuLi in hexanes was added at −60° C. This mixture was stirred for 4.5 h at room temperature, then cooled to −60° C., and 4.78 g (12.7 mmol) of ZrCl$_4$(THF)$_2$ was added. The resulting mixture was stirred for 24 h at room temperature and then evaporated to dryness. To orange-red crystalline residue 150 ml of toluene was added. This mixture was heated to 70° C., filtered through glass frit (G3), and the filtrate evaporated to ca. 35 ml. Further on, 65 ml of hexanes was added. The suspension formed was heated to dissolve the precipitate. Red crystals precipitated from this mixture at room temperature were collected and dried in vacuum. This procedure gave 1.06 g (10%) of pure meso-complex. The mother liquid was evaporated to ca. 40 ml, heated to dissolve the precipitate formed. Orange crystals precipitated from this solution at −30° C. were collected, dried in vacuum. Yield 3.01 g (27%) of rac-complex including ca. 3% of meso-complex which can be additionally purified via crystallization from hexanes-toluene (1:1, vol.) to give analytically pure rac-complex as solvate with toluene. On the evidence of NMR spectroscopy, this sample included 0.88 toluene molecule per metallocene molecule. The mother liquid was evaporated to dryness, and then 40 ml of hexanes was added. The formed suspension was heated to 70° C., cooled to room temperature, and then filtered through glass frit (G3). The precipitate was dried in vacuum. This procedure gave 1.40 g (12%) of a ca. 1:3 mixture of rac- and meso-complexes. Crystals precipitated from the hexanes filtrate at −30° C. were collected and dried in vacuum. This procedure gave 0.80 g (7%) of pure rac-complex. Thus, the overall yield of rac- and meso-complexes was found to be over 56%.

rac-Dimethylsilylene-bis(6-tert-butyl-2-isobutyl-5-methoxy-4-phenyl-1H-inden-1-yl)zirconium dichloride, toluene solvate (0.88 C$_7$H$_8$)

Anal. calc. for C$_{56.16}$H$_{70.04}$Cl$_2$O$_2$SiZr: C, 69.80; H, 7.31. Found: C, 69.86; H, 7.26.

$^1$H NMR (CD$_2$Cl$_2$): δ 7.61 (br.m, 4H, 2,6-H in Ph of the complex), 7.54 (s, 2H, 7-H in indenyl), 7.44 (m, 4H, 3,5-H in Ph of the complex), 7.35 (m, 2H, 4-H in Ph of the complex), 7.12-7.25 (m, 0.88×5H, Ph in toluene), 6.55 (s, 2H, 3-H in indenyl), 3.35 (s, 6H, OMe), 2.61 (dd, J=13.6 Hz, J=7.2 Hz, 2H, CHH'CH$_2$Me$_2$), 2.34 (s, 0.88×3H, Me in toluene), 2.03 (dd, J=13.6 Hz, J=7.3 Hz, 2H, CHH'CH$_2$Me$_2$), 1.64 (m, 2H, CHMe$_2$), 1.40 (s, 18H, $^t$Bu), 1.31 (s, 6H, SiMe$_2$), 0.84 (d, J=6.6 Hz, 6H, CHMeMe'), 0.76 (d, J=6.6 Hz, 6H, CHMeMe'). $^{13}$C NMR (CD$_2$Cl$_2$): δ 161.5, 145.6, 142.0, 138.6, 135.2, 131.4, 130.0, 128.9, 128.5, 124.7, 123.0, 121.4, 83.4, 64.0, 43.5, 37.3, 34.1, 31.7, 23.8, 23.5, 5.0.

meso-Dimethylsilylene-bis(6-tert-butyl-2-isobutyl-5-methoxy-4-phenyl-1H-inden-1-yl)zirconium dichloride Anal. calc. for C$_{50}$H$_{62}$Cl$_2$O$_2$SiZr: C, 67.84; H, 7.06. Found: C, 67.93; H, 7.00.

$^1$H NMR (CD$_2$Cl$_2$): δ 7.64 (br.m, 4H, 2,6-H in Ph), 7.49 (s, 2H, 7-H in indenyl), 7.45 (m, 4H, 3,5-H in Ph), 7.36 (m, 2H, 4-H in Ph), 6.50 (s, 2H, 3-H in indenyl), 3.19 (s, 6H, OMe), 2.68 (dd, J=13.4 Hz, J=7.8 Hz, 2H, CHH'CH$_2$Me$_2$), 2.47 (dd, J=13.4 Hz, J=6.6 Hz, 2H, CHH'CH$_2$Me$_2$), 1.64 (m, 2H, CHMe$_2$), 1.44 (s, 3H, SiMeMe'), 1.38 (s, 18H, $^t$Bu), 1.19 (s, 3H, SiMeMe'), 0.82 (d, J=6.7 Hz, 6H, CHMeMe'), 0.80 (d, J=6.7 Hz, 6H, CHMeMe'). $^{13}$C NMR (CD$_2$Cl$_2$): δ 159.5, 145.6, 142.4, 138.4, 136.2, 131.4, 130.0, 128.9, 128.3, 127.3, 123.3, 122.4, 85.8, 63.6, 43.4, 37.2, 34.6, 32.0, 23.9, 23.3, 6.2, 4.1.

Example 2

Manufacture of rac-Dimethyl silylene-bis(6-tert-butyl-2-(2,2-dimethylpropyl)-5-methoxy-4-phenyl-1H-inden-1-yl)zirconium dichloride Diethyl (2,2-dimethylpropylidene)malonate

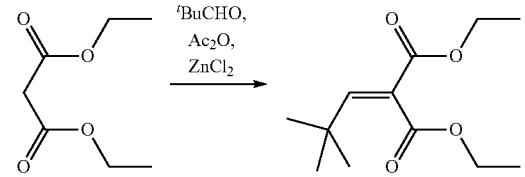 [SMILES: CCOC(=O)CC(=O)OCC ; CCOC(=O)C(=CC(C)(C)C)C(=O)OCC]

In 1-liter flask, to a mixture of 320 g (2.0 mol) of diethyl malonate, 172 g (2.0 mol) of pivalaldehyde, and 256 g (2.51 mol) of acetic anhydride 38.4 g (0.28 mol) of ZnCl$_2$ was added in one portion by vigorous stirring. This mixture was spontaneously warmed to ca. 105° C. The formed red mixture was refluxed for 36 h, then cooled to ambient temperature, and 800 ml of toluene was added. This solution was washed by 3×500 ml of water. The combined aqueous solution was extracted with 2×350 ml of toluene. The combined toluene extract and solution was dried over K$_2$CO$_3$, passed through ca. 7 cm layer of silica gel 60 (40-63 um) on glass frit, and then evaporated to dryness. Fractional rectification of the residue gave yellowish oil of the title product, b.p. 132-135° C./20 mm Hg. Yield 254 g (56%).

Anal. calc. for C$_{12}$H$_{20}$O$_4$: C, 63.14; H, 8.83. Found: C, 63.19; H, 8.85.

$^1$H NMR (CDCl$_3$): δ 6.84 (s, 1H, CH$^t$Bu), 4.24 (q, J=7.1 Hz, 2H, CH$_2$Me), 4.18 (q, J=7.1 Hz, 2H, CH$_2$Me), 1.29 (t, J=7.1 Hz, 3H, CH$_2$Me), 1.24 (t, J=7.1 Hz, 3H, CH$_2$Me), 1.11 (s, 9H, $^t$Bu). $^{13}$C NMR (CDCl$_3$): δ 166.9, 164.4, 154.9, 125.3, 61.3, 61.2, 34.1, 28.8, 14.0, 13.9.

Diethyl (2,2-dimethylpropyl)malonate

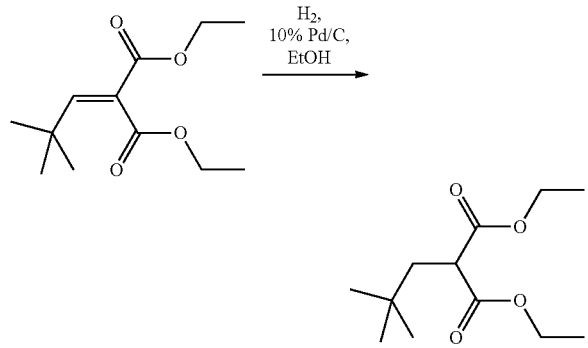

In 2-liter stainless steel pressure reactor, to a solution of 114 g (0.50 mol) of diethyl (2,2-dimethylpropylidene)malonate in 650 ml of ethanol 1.60 g of 10% Pd/C was added. Hydrogenation was carried at 5 atm of hydrogen gas for 6 h at 40° C. The following GC analysis showed that conversion of the starting material into the title product was almost quantitative. The reaction mixture was added to 1500 cm$^3$ of cold water, and the product was extracted by 3×300 ml of dichloromethane. The combined organic extract was passed through short layer of silica gel 60 (40-63 um), evaporated in vacuum, and then used without an additional purification. Yield of the title material was almost quantitative.

Anal. calc. for C$_{12}$H$_{22}$O$_4$: C, 62.58; H, 9.63. Found: C, 62.80; H, 9.78.

$^1$H NMR (CDCl$_3$): δ 4.16 (q, J=7.1 Hz, 4H, CH$_2$Me), 3.35 (t, J=6.3 Hz, 1H, CH$_2$CH), 1.90 (d, J=6.3 Hz, 2H, $^t$BuCH$_2$), 1.24 (t, J=7.1 Hz, 6H, CH$_2$Me), 0.87 (s, 9H, $^t$Bu). $^{13}$C NMR (CDCl$_3$): δ 170.3, 61.3, 48.8, 41.8, 30.4, 29.0, 14.0.

(2,2-Dimethylpropyl)malonic acid

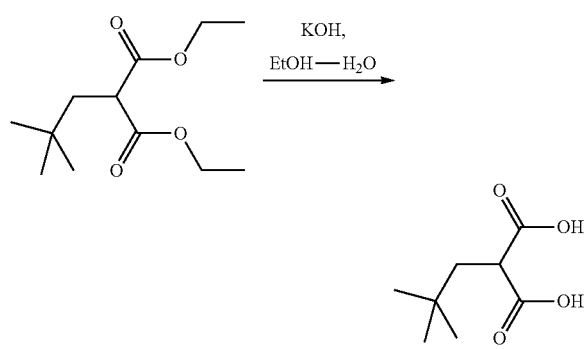

To a solution of the above-obtained diethyl (2,2-dimethylpropyl)malonate on 500 cm$^3$ of methanol a solution of 125 g of KOH in 1000 cm$^3$ of water was added. The obtained mixture was refluxed for 5 h, and then methanol and ethanol were distilled off at atmospheric pressure. To the residue ca. 3000 cm$^3$ of water was added, the obtained solution was acidified by saturated HCl to pH 1. The formed product was extracted with 3×500 ml of ether. To the combined extract 200 ml of toluene was added, and the obtained solution was evaporated in vacuum to give a ca. 3 to 1 mixture of the title product and toluene (on the evidence of NMR spectroscopy). This mixture was further used without an additional purification.

$^1$H NMR (CDCl$_3$): δ 12.1 (br.s, 2H, CO$_2$H), 3.51 (t, J=6.3 Hz, 1H, CH$_2$CH), 2.0 (d, J=6.3 Hz, 2H, CH$_2$CH), 0.97 (s, 9H, $^t$Bu). $^{13}$C NMR (CDCl$_3$): δ 176.4, 48.6, 41.8, 30.6, 28.9.

2-(2,2-Dimethylpropyl)acrylic acid

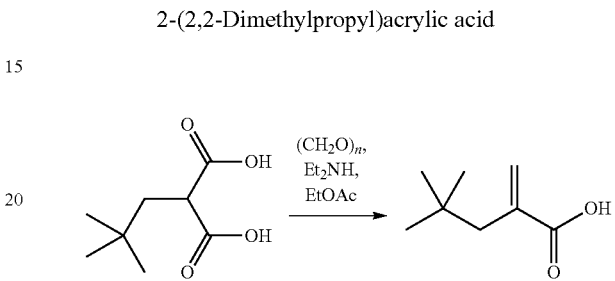

To a solution of the above-obtained (2,2-dimethylpropyl)malonic acid (0.50 mol given almost quantitative yields on the hydrogenation and saponification stages) in 750 ml of ethyl acetate 60.0 ml (42.4 g, 0.58 mol) of diethylamine was added dropwise by vigorous stirring at 5° C. Further on, 21.1 g (0.702 mmol) of paraform was added, and the formed mixture was refluxed for 6 h, then cooled to 5° C., and, finally, 500 ml of ether and 800 ml of 4.5 N HCl were added. After shaking for 30 sec the organic layer was separated, the aqueous layer was extracted with 2×300 ml of ether. The combined organic extract was dried over Na$_2$SO$_4$ and then evaporated to dryness. Fractional rectification of the residue gave colorless oil (b.p. 120-122° C./20 mm Hg) which crystallizes on storage at room temperature. Yield 62 g (87%) of the title compound.

Anal. calc. for C$_8$H$_{14}$O$_2$: C, 67.57; H, 9.92. Found: C, 67.49; H, 9.96.

$^1$H NMR (CDCl$_3$): δ 11.9 (br.s, 1H, CO$_2$H), 6.36 (m, 1H, HH'C=), 6.58 (m, 1H, HH'C=), 2.26 (s, 2H, $^t$BuCH$_2$), 0.89 (s, 9H, $^t$Bu). $^{13}$C NMR (CDCl$_3$): δ 173.9, 138.1, 129.7, 43.8, 31.5, 29.1.

6-tert-Btyl-2-(2,2-dimethylpropyl)-5-methoxy-1-indanone and 6-tert-butyl-2-(2,2-dimethylpropyl)-7-methoxy-1-indanone

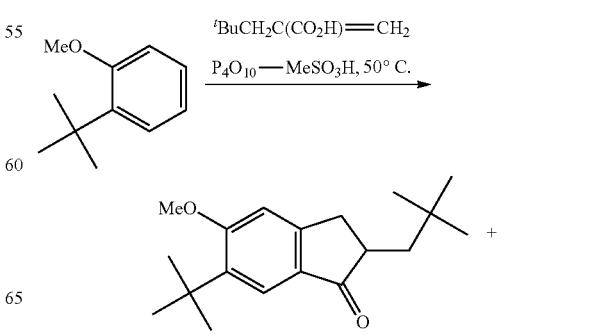

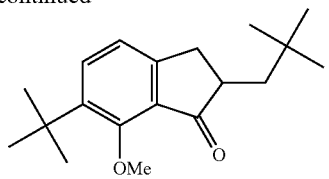

To Iton reagent obtained from 110 g of $P_4O_{10}$ and 560 ml of methanesulfonic acid a mixture of 62.3 g (0.379 mol) of 1-tert-butyl-2-methoxybenzene and 59.9 g (0.421 mol) of 2-(2,2-dimethylpropyl)acrylic acid was added dropwise by vigorous stirring for ca. 40 min at 50° C. The resulting mixture was stirred for additional 40 min at this temperature and then poured on a mixture of 1000 cm³ of ice and 1000 cm³ of cold water. The product was extracted by 3×250 ml of dichloromethane. The combined organic extract was washed by aqueous $K_2CO_3$, filtered through glass frit (G3), and evaporated to dryness. The residue was dissolved in 220 ml of hexanes. Crystalline solid precipitated from this solution at 5° C. was filtered off, washed by 2×150 ml of hexanes, and dried in vacuum. This procedure gave 51.9 g of white solid as a ca. 5 to 1 mixture of 6-tert-butyl-2-(2,2-dimethylpropyl)-5-methoxy-1-indanone and 6-tert-butyl-2-(2,2-dimethylpropyl)-7-methoxy-1-indanone. These isomers were separated by flash chromatography on silica gel 60 (40-63 um, 1500 cm³ of silica gel, eluent: hexanes-dichloromethane-ether=20: 10:1, vol.). This procedure gave 42.4 g (39%) of 6-tert-butyl-2-(2,2-dimethylpropyl)-5-methoxy-1-indanone and 8.47 g (8%) of 6-tert-butyl-2-(2,2-dimethylpropyl)-7-methoxy-1-indanone. Additional quantity of the products was isolated from mother liquid by flash chromatography on silica gel 60 followed by crystallization of the crude products from hexanes. This procedure gave additional 4.38 g (4%) of 6-tert-butyl-2-(2,2-dimethylpropyl)-5-methoxy-1-indanone and 12.0 g (11%) of 6-tert-butyl-2-(2,2-dimethylpropyl)-7-methoxy-1-indanone. Thus, the overall yields were 43 and 19% for 5- and 7-methoxy-substituted products, respectively.

6-tert-Butyl-2-(2,2-dimethylpropyl)-5-methoxy-1-indanone

Anal. calc. for $C_{19}H_{28}O_2$: C, 79.12; H, 9.78. Found: C, 79.29; H, 9.85.

¹H NMR (CDCl₃): δ 7.67 (s, 1H, 7-H in indanone), 6.85 (s, 1H, 4-H in indanone), 3.91 (s, 3H, OMe), 3.33 (dd, J=17.1 Hz, J=7.6 Hz, 1H, 3-HH' in indanone), 2.75 (dd, J=17.1 Hz, J=3.8 Hz, 1H, 3-CHH' in indanone), 2.56 (m, 1H, 2-CH in indanone), 2.07 (dd, J=13.8 Hz, J=1.5 Hz, 1H, CHH'ᵗBu), 1.36 (s, 9H, 6-ᵗBu in indanone), 1.18 (dd, J=13.8 Hz, J=10.7 Hz, 1H, CHH'ᵗBu), 0.99 (s, 9H, ᵗBuCH₂). ¹³C NMR (CDCl₃): δ 208.0, 164.6, 154.8, 138.7, 128.9, 122.0, 107.6, 55.2, 46.0, 45.2, 35.8, 35.1, 31.0, 29.9, 29.6.

6-tert-Butyl-2-(2,2-dimethylpropyl)-7-methoxy-1-indanone

Anal. calc. for $C_{19}H_{28}O_2$: C, 79.12; H, 9.78. Found: C, 79.33; H, 9.90.

¹H NMR (CDCl₃): δ 7.51 (d, J=8.7 Hz, 1H, 5-H in indanone), 6.72 (d, J=8.7 Hz, 1H, 4-H in indanone), 3.90 (s, 3H, OMe), 3.59 (dd, J=16.8 Hz, J=7.9 Hz, 1H, 3-HH' in indanone), 2.91 (dd, J=16.8 Hz, J=4.7 Hz, 1H, 3-CHH' in indanone), 2.53 (m, 1H, 2-CH in indanone), 2.10 (dd, J=13.9 Hz, J=2.1 Hz, 1H, CHH'ᵗBu), 1.39 (s, 9H, 6-ᵗBu in indanone), 1.19 (dd, J=13.9 Hz, J=10.1 Hz, 1H, CHH'ᵗBu), 1.00 (s, 9H, ᵗBuCH₂). ¹³C NMR (CDCl₃): δ 207.0, 156.3, 153.5, 139.1, 133.2, 125.1, 108.8, 55.6, 45.7, 45.0, 37.7, 35.1, 30.9, 30.7, 29.9.

4-Bromo-6-tert-butyl-2-(2,2-dimethylpropyl)-5-methoxy-1-indanone

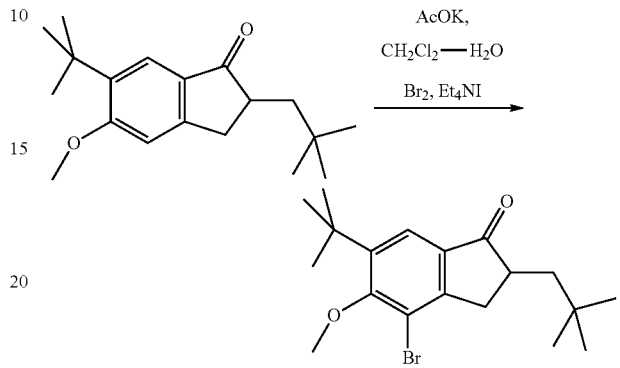

To a mixture of 42.4 g (0.146 mol) of 6-tert-butyl-2-(2,2-dimethylpropyl)-5-methoxy-1-indanone, 58.0 g (0.426 mol) of sodium acetate, trihydrate, 0.93 g of Et₄NI, 130 ml of dichloromethane, and 250 ml of water 23.5 g (0.147 mol) of bromine was added dropwise by vigorous stirring for 5 min at 5° C. The resulting mixture was stirred for additional 1 h at this temperature. Further on, this mixture was washed by aqueous Na₂SO₃ to remove an excess of bromine, and then 500 ml of dichloromethane was added. The organic layer was separated, and the aqueous layer was extracted with 2×250 ml of dichloromethane. The combined organic extract was dried over $K_2CO_3$ and then evaporated to dryness to give 54.8 g of yellowish oil which crystallizes on storage at room temperature. This product was further used without an additional purification.

Anal. calc. for $C_{19}H_{27}BrO_2$: C, 62.13; H, 7.41. Found: C, 62.32; H, 7.55.

¹H NMR (CDCl₃): δ 7.68 (s, 1H, 7-H in indanone), 4.00 (s, 3H, OMe), 3.32 (dd, J=17.5 Hz, J=7.8 Hz, 1H, 3-HH' in indanone), 2.69 (dd, J=17.4 Hz, J=4.0 Hz, 1H, 3-CHH' in indanone), 2.59 (m, 1H, 2-CH in indanone), 2.06 (dd, J=13.9 Hz, J=1.8 Hz, 1H, CHH'ᵗBu), 1.38 (s, 9H, 6-ᵗBu in indanone), 1.22 (dd, J=13.9 Hz, J=10.5 Hz, 1H, CHH'ᵗBu), 1.01 (s, 9H, ᵗBuCH₂). ¹³C NMR (CDCl₃): δ 208.0, 162.7, 154.2, 145.4, 132.8, 121.4, 116.5, 61.6, 45.9, 45.3, 37.2, 35.7, 30.9, 30.6, 29.9.

6-tert-Butyl-2-(2,2-dimethylpropyl)-5-methoxy-4-phenyl-1-indanone and 6-tert-butyl-2-(2,2-dimethylpropyl)-5-hydroxy-4-bromo-1-indanone

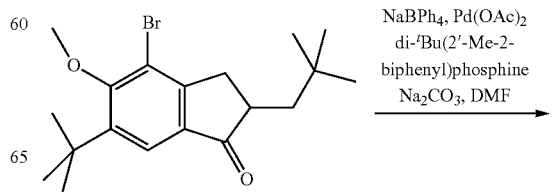

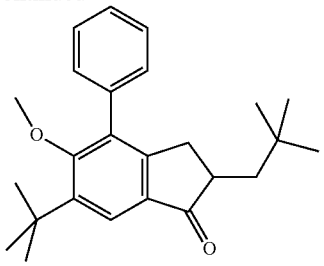

To a mixture of 54.8 g (0.147 mol) of 4-bromo-6-tert-butyl-2-(2,2-dimethylpropyl)-5-methoxy-1-indanone, 30.0 g (0.088 mol) of NaBPh$_4$, 75.0 g of Na$_2$CO$_3$, and 600 ml of DMF a mixture of 446 mg (1.99 mmol, 1.33 mol. %) of Pd(OAc)$_2$ and 928 mg (2.97 mml, 1.99 mol. %) of di-tert-butyl(2'-methyl-2-biphenylyl)phosphine was added in one portion. The resulting mixture was refluxed for 7 h, cooled to room temperature, and DMF was distilled off in vacuum. The residue was dissolved in 500 ml of dichloromethane, and the obtained solution was passed through short layer of silica gel 60. This silica gel layer was additionally washed by 2×100 ml of dichloromethane. The product was extracted with 5×1 liter of dichloromethane. The combined organic extract was evaporated to dryness. Crude product with Rf~0.2 was isolated by flash chromatography on silica gel 60 (40-63 um, 1500 cm$^3$ of silica gel, eluent: hexanes-dichloromethane-ether=1500:500:10, vol.). This procedure gave ca. 40 g of white solid which is a mixture of the desired product, 6-tert-butyl-2-(2,2-dimethylpropyl)-5-methoxy-4-phenyl-1-indanone, and demethylation product, 6-tert-butyl-2-(2,2-dimethylpropyl)-5-hydroxy-4-phenyl-1-indanone. This mixture was dissolved in 200 ml of hot hexanes, crystals precipitated from this solution at room temperature were collected, washed by 10 ml of cold hexanes, and dried in vacuum. This procedure gave 9.20 g (18%) of tert-butyl-2-(2,2-dimethylpropyl)-5-hydroxy-4-phenyl-1-indanone. The mother liquid was evaporated to dryness to give 19.7 g of 6-tert-butyl-2-(2,2-dimethylpropyl)-5-methoxy-4-phenyl-1-indanone of 93% purity (on the evidence of NMR spectroscopy). Therefore, the target material was obtained in 39% yield.

6-tert-Butyl-2-(2,2-dimethylpropyl)-5-methoxy-4-phenyl-1-indanone $^1$H NMR (CDCl$_3$): δ 7.75 (s, 1H, 7-H in indanone), 7.47 (m, 2H, 3,5-H in Ph), 7.36-7.43 (m, 3H, 2,4,6-H in Ph), 3.26 (s, 3H, OMe), 3.13 (dd, J=17.1 Hz, J=7.4 Hz, 1H, 3-HH' in indanone), 2.57 (dd, J=17.1 Hz, J=4.0 Hz, 1H, 3-CHH' in indanone), 2.52 (m, 1H, 2-CH in indanone), 2.07 (dd, J=13.9 Hz, J=1.4 Hz, 1H, CHH"Bu), 1.42 (s, 9H, 6-$^t$Bu in indanone), 1.21 (dd, J=13.9 Hz, J=9.9 Hz, 1H, CHH"Bu), 0.93 (s, 9H, $^t$BuCH$_2$). $^{13}$C NMR (CDCl$_3$): δ 208.6, 163.4, 152.9, 143.4, 136.4, 132.4, 131.2, 129.6, 128.7, 127.5, 121.4, 60.5, 45.8, 45.3, 35.4, 30.9, 30.5, 29.9, 29.3.

6-tert-Butyl-2-(2,2-dimethylpropyl)-5-hydroxy-4-bromo-1-indanone

Anal. calc. for C$_{24}$H$_{30}$O$_2$: C, 82.24; H, 8.63. Found: C, 82.30; H, 7.71.

$^1$H NMR (CDCl$_3$): δ 7.65 (s, 1H, 7-H in indanone), 6.36 (s, 1H, OH), 3.28 (dd, J=17.5 Hz, J=7.6 Hz, 1H, 3-HH' in indanone), 2.68 (dd, J=17.5 Hz, J=3.8 Hz, 1H, 3-CHH' in indanone), 2.60 (m, 1H, 2-CH in indanone), 2.07 (dd, J=13.9 Hz, J=1.3 Hz, 1H, CHH"Bu), 1.40 (s, 9H, 6-$^t$Bu in indanone), 1.21 (dd, J=13.9 Hz, J=10.6 Hz, 1H, CHH"Bu), 1.01 (s, 9H, $^t$BuCH$_2$). $^{13}$C NMR (CDCl$_3$): δ 207.3, 156.3, 152.9, 138.1, 130.4, 121.8, 110.2, 46.0, 45.2, 36.9, 35.6, 31.0, 29.9, 29.3.

5-tert-Butyl-2-(2,2-dimethylpropyl)-6-methoxy-7-phenyl-1H-indene (966__7)

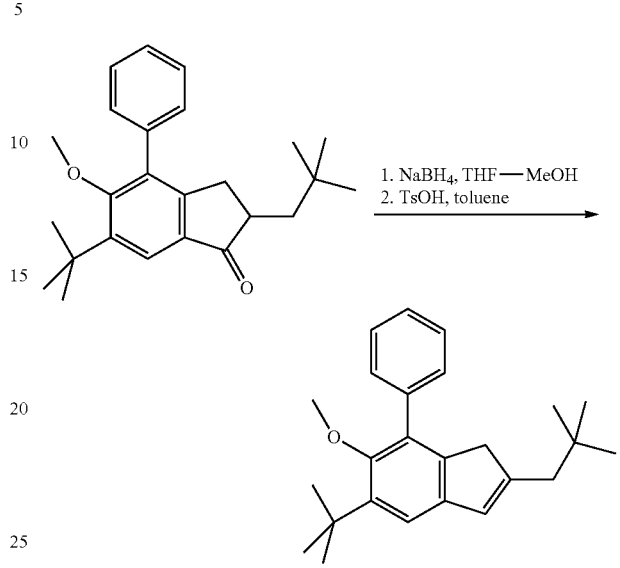

To a mixture of 19.7 g of 6-tert-butyl-2-(2,2-dimethylpropyl)-5-methoxy-4-phenyl-1-indanone of 93% purity (50.3 mmol), 15.0 g of NaBH$_4$, and 200 ml of THF 100 ml of water was slowly (for ca. 10 h) added by vigorous stirring at 5° C. The resulting mixture was stirred overnight at room temperature. Further on, 500 ml of cold water was added, the resulting mixture was acidified by 12 N HCl to pH 1, and then the crude product was extracted with 3×150 ml of dichloromethane. To a solution of the residue in 300 ml of toluene 0.5 g of TsOH was added, the resulting mixture was refluxed for 15 min with Dean-Stark head, then quickly cooled to room temperature, and treated with 50 ml of 10% aqueous K$_2$CO$_3$ to remove acidic impurities. The organic layer was separated, the aqueous layer was extracted with 2×75 ml of dichloromethane. The combined organic extract was dried over K$_2$CO$_3$ and then evaporated to dryness. The product was isolated by flash-chromatography on silica gel 60 (40-64 um, 450 m$^3$ of silica gel, eluent: hexanes-dichloromethane=4:1, vol.). Yield 17.3 g (99%) of the title product as yellowish oil.

Anal. calc. for C$_{25}$H$_{32}$O: C, 86.15; H, 9.25. Found: C, 86.24; H, 9.38.

$^1$H NMR (CDCl$_3$): δ 7.47-7.52 (m, 2H, 2,6-H in Ph), 7.44 (m, 2H, 3,5-H in Ph), 7.34 (m, 1H, 4-H in Ph), 7.27 (s, 1H, 4-H in indene), 6.49 (s, 1H, 3-H in indene), 3.20-3.23 (m, 5H, OMe and 1,1'-H in indene), 2.29 (s, 2H, CH$_2$$^t$Bu), 1.44 (s, 3H, 5-$^t$Bu in indene), 0.92 (s, 3H, CH$_2$$^t$Bu). $^{13}$C NMR (CDCl$_3$): δ 154.4, 147.5, 141.8, 141.1, 140.6, 138.4, 131.5, 129.6, 129.3, 128.4, 126.9, 117.4, 60.7, 45.2, 43.7, 35.2, 31.8, 31.0, 29.9.

Bis(5-tert-butyl-2-(2,2-dimethylpropyl)-6-methoxy-7-phenyl-1H-inden-3-yl)(dimethyl)silane

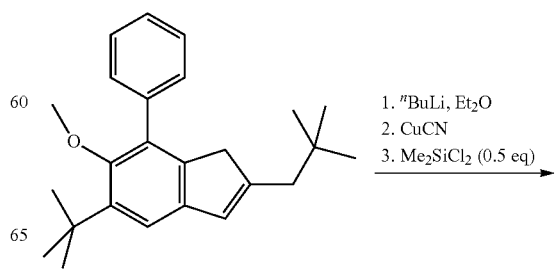

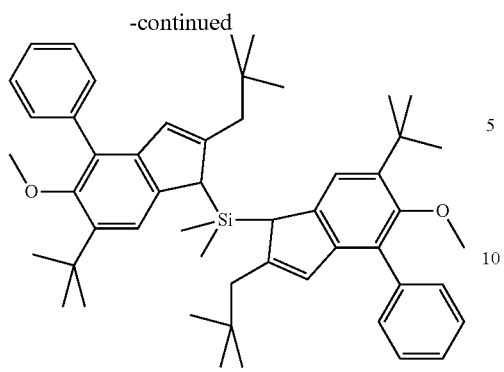 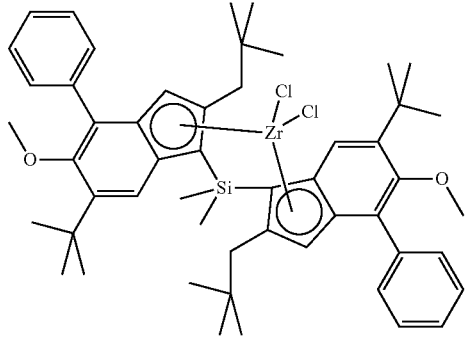

To a solution of 17.3 g (49.7 mmol) of 5-tert-butyl-2-(2,2-dimethylpropyl)-6-methoxy-7-phenyl-1H-indene in 450 ml of ether 19.9 ml (49.8 mmol) of 2.5 M "BuLi in hexanes was added at −50° C. This mixture was stirred for 12 h at ambient temperature, then cooled to −50° C., and 0.20 g of CuCN was added. The resulting mixture was warmed to −20° C., and 3.21 g (24.9 mmol) of $Me_2SiCl_2$ was added in one portion. This mixture was stirred overnight at room temperature, then 1 ml of water was added, and the resulting mixture was passed through short layer of silica gel 60 (40-63 um). The silica gel layer was additionally washed by 3×75 ml of dichloromethane. The filtrate was evaporated to dryness to give 18.2 g (97%) of the title compound as yellowish solid.

Anal. calc. for $C_{52}H_{68}O_2Si$: C, 82.92; H, 9.10. Found: C, 83.11; H, 9.23.

$^1$H NMR ($CDCl_3$): δ 7.32-7.68 (m, 14H, Ph and 7-H in indenyl of rac- and meso-compounds), 6.45 (s, 2H, 3-H in indenyl of meso-compound), 6.33 (s, 2H, 3-H in indenyl of rac-compound), 3.90 (s, 2H, 1-H in indenyl of rac-compound), 3.84 (s, 2H, 1-H in indenyl of meso-compound), 3.25 (s, 6H, OMe in rac-compound), 3.23 (s, 6H, OMe in meso-compound), 2.42 (d, J=13.1 Hz, 2H, CHH''Bu in meso-compound), 2.27 (d, J=13.1 Hz, 2H, CHH''Bu in meso-compound), 2.02 (d, J=13.6 Hz, 2H, CHH''Bu in rac-compound), 1.94 (d, J=13.6 Hz, 2H, CHH''Bu in rac-compound), 1.46 (s, 18H, 6-'Bu in indenyl in rac-compound), 1.45 (s, 18H, 6-'Bu in indenyl in meso-compound), 0.89 (s, 18H, 'BuCH$_2$ in meso-compound), 0.77 (s, 18H, 'BuCH$_2$ in rac-compound), −0.11 (s, 6H, SiMeMe' in meso-compound), −0.14 (s, 6H, SiMe$_2$ in rac-compound), −0.48 (s, 6H, SiMeMe' in meso-compound).

Rac- and meso-Dimethylsilylene-bis(6-tert-butyl-2-(2,2-dimethylpropyl)-5-methoxy-4-phenyl-1H-inden-1-yl)zirconium dichloride

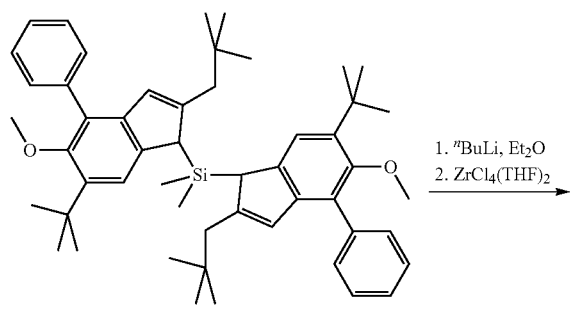

1. "BuLi, Et$_2$O
2. ZrCl$_4$(THF)$_2$

To a solution of 18.2 g (24.2 mmol) of bis(5-tert-butyl-2-(2,2-dimethylpropyl)-6-methoxy-7-phenyl-1H-inden-3-yl)(dimethyl)silane in 250 ml of ether 19.3 ml (48.3 mmol) of 2.5 M "BuLi in hexanes was added at −78° C. This mixture was stirred overnight at room temperature, cooled to −60° C., and then 9.12 g (24.2 mmol) of ZrCl$_4$(THF)$_2$ was added. The resulting mixture was stirred for 24 h at room temperature to give carroty solution which was then evaporated to drynedd. To the residue 200 ml of toluene was added. The obtained mixture was evaporated to ca. 100 ml, added 100 ml of toluene, then hot (70° C.) suspension was filtered through glass frit (G3). The filtrate was evaporated to ca. 100 ml, and 100 ml of n-octane was added. The resulting solution was evaporated to ca. 100 ml. The formed precipitate was filtered off, dried in vacuum. This procedure gave 2.20 g (10%) of pure meso-Dimethylsilylene-bis(6-tert-butyl-2-(2,2-dimethylpropyl)-5-methoxy-4-phenyl-1H-inden-1-yl)zirconium dichloride. The filtrate was evaporated to dryness, the residue was crystallized from 100 ml of hot n-octane. Crystals precipitated at room temperature were collected and dried in vacuum. This procedure gave 5.06 g (23%) of orange crystalline rac-Dimethylsilylene-bis(6-tert-butyl-2-(2,2-dimethylpropyl)-5-methoxy-4-phenyl-1H-inden-1-yl)zirconium dichloride contaminated with ca. 7% of meso-Dimethylsilylene-bis(6-tert-butyl-2-(2,2-dimethylpropyl)-5-methoxy-4-phenyl-1H-inden-1-yl)zirconium dichloride. The filtrate was evaporated to ca. 50 ml, heated to dissolve the precipitate formed, crystals precipitated at −30° C. were collected, dried in vacuum. This procedure gave 1.42 g (6%) of rac-Dimethylsilylene-bis(6-tert-butyl-2-(2,2-dimethylpropyl)-5-methoxy-4-phenyl-1H-inden-1-yl)zirconium dichloride including ca. 5% of some impurity but not meso-isomer. The above-described 5.06 g rac-Dimethylsilylene-bis(6-tert-butyl-2-(2,2-dimethylpropyl)-5-methoxy-4-phenyl-1H-inden-1-yl)zirconium dichloride contaminated with ca. 7% of meso-Dimethylsilylene-bis(6-tert-butyl-2-(2,2-dimethylpropyl)-5-methoxy-4-phenyl-1H-inden-1-yl)zirconium dichloride was additionally recrystallized from hot n-octane-toluene (10:1, vol.) to give 1.14 g of analytically pure rac-Dimethylsilylene-bis(6-tert-butyl-2-(2,2-dimethylpropyl)-5-methoxy-4-phenyl-1H-inden-1-yl)zirconium dichloride.

rac-Dimethylsilylene-bis(6-tert-butyl-2-(2,2-dimethylpropyl)-5-methoxy-4-phenyl-1H-inden-1-yl)zirconium dichloride Anal. calc. for $C_{52}H_{66}Cl_2O_2SiZr$: C, 68.39; H, 7.28. Found: C, 68.45; H, 7.40.

$^1$H NMR ($CDCl_3$): c 7.66 (m, 4H, 2,6-H in Ph), 7.56 (s, 2H, 7-H in indenyl), 7.46 (m, 4H, 3,5-H in Ph), 7.34 (m, 2H, 4-H in Ph), 6.59 (s, 2H, 3-H in indenyl), 3.42 (s, 6H, OMe), 2.75

(d, J=13.4 Hz, 2H, ′BuCHH′), 2.08 (d, J=13.4 Hz, 2H, ′BuCHH′), 1.44 (s, 18H, 6-′Bu in indenyl), 1.36 (s, 6H, SiMe$_2$), 0.84 (s, 18H, ′BuCH$_2$). $^{13}$C NMR (CDCl$_3$): δ 159.9, 144.0, 138.9, 136.9, 133.7, 129.8, 128.5, 127.2, 127.1, 122.7, 121.1, 120.4, 82.2, 62.6, 45.8, 35.9, 33.2, 30.4, 29.8, 5.34.

meso-Dimethylsilylene-bis(6-tert-butyl-2-(2,2-dimethylpropyl)-5-methoxy-4-phenyl-1H-inden-1-yl) zirconium dichloride Anal. calc. for C$_{52}$H$_{66}$Cl$_2$O$_2$SiZr: C, 68.39; H, 7.28. Found: C, 68.52; H, 7.39.

$^1$H NMR (CDCl$_3$): δ 7.64 (m, 4H, 2,6-H in Ph), 7.39-7.47 (m, 6H, 3,5-H in Ph and 7-H in indenyl), 7.31 (m, 2H, 4-H in Ph), 6.49 (s, 2H, 3-H in indenyl), 3.20 (s, 6H, OMe), 2.82 (d, J=13.3 Hz, 2H, ′BuCHH′), 2.43 (d, J=13.3 Hz, 2H, ′BuCHH′), 1.42 (s, 3H, SiMeMe′), 1.37 (s, 18H, 6-′Bu in indenyl), 1.22 (s, 3H, SiMeMe′), 0.80 (s, 18H, ′BuCH$_2$).

Catalyst Example 1 (E1) of Example 1

Inside the glovebox, 80 µL of dry and degassed surfactant solution were mixed with 2 mL of MAO in a septum bottle and left to react overnight. The following day, 73.4 mg of the metallocene toluene solvate (0.076 mmol, 1 equivalent, 67.2 mg of metallocene+6.2 mg of toluene) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately (measured emulsion stability=13 seconds) and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.39 g of a red free flowing powder was obtained.

Catalyst Example 2 (E2)

The catalyst Example 2 was prepared according to the method described for Catalyst Example 1 using 69.5 mg of rac-dimethylsilylene-bis(6-tert-butyl-2-(2,2-dimethylpropyl)-5-methoxy-4-phenyl-1H-inden-1-yl)zirconium dichloride. 0.68 g of a red free flowing powder was obtained.

Comparative Example 1 (C1)

rac-cyclohexyl(methyl)silyl-bis[2-methyl-4-(4′-tert-butylphenyl)indenyl]zirconium dichloride (CAS-888227, WO2006/060544)

The C1 catalyst was synthesised according to the above described recipe using the above metallocene.

Comparative Example 2 (C2)

rac-dimethylsilyl-bis[2-methyl-4-phenylindenyl] zirconium dichloride (CAS-153882-67-8)

The C2 catalyst was synthesized according to the above described recipe using the above metallocene.

TABLE 1

Catalyst syntheses summary

| Catalyst | Al/Zr (recipe) | Yield | Al (%) | Zr (%) | Al/Zr (molar) |
|---|---|---|---|---|---|
| E1 | 300 | 0.39 g | 28.7 | 0.33 | 294 |
| E2 | 300 | 0.68 g | 25.8 | 0.31 | 281 |
| C1 | 300 | 1.2 g | 31.0 | 0.37 | 283 |
| C2 | 300 | 0.46 g | 25.5 | 0.38 | 227 |

Polymerisations: homopolymerisation of propylene and random co-polymerisation of propylene and ethylene The polymerisation experiments were performed in a 5 L reactor. 200 µl of triethylaluminum was fed as a scavenger in 5 mL of dry and degassed pentane. The desired amount of hydrogen was then loaded (measured in mmol) and 1100 g of liquid propylene was fed into the reactor followed by the desired amount of ethylene (fed into the gas phase) when ethylene was used as the comonomer. The temperature was set to 30° C. The desired amount of catalyst in 5 mL of PFC was flushed into the reactor with a nitrogen overpressure. The temperature was then raised to 70° C. over a period of 15 minutes. The polymerisation was stopped after 30 minutes by venting the reactor and flushing with nitrogen before the polymer is collected. Results are presented in the tables which follow.

TABLE 2

Homopolymerisation examples

| Catalyst | Exp. | Cat (mg) | Temp. (° C.) | Time (min.) | H$_2$ (mmol) | Polymer (g) | Activity (kg/g/h) | Metal activity (kg/g Zr/h) |
|---|---|---|---|---|---|---|---|---|
| E1 | P1 | 12.9 | 70.0 | 30.0 | 1.0 | 158 | 24.5 | 7424 |
| E1 | P2 | 4.8 | 70.0 | 30.0 | 6.0 | 117 | 48.8 | 14788 |
| E1 | P3 | 7.4 | 70.0 | 30.0 | 15.0 | 220 | 59.5 | 18030 |
| E2 | P4 | 10.2 | 70.0 | 30.0 | 1.0 | 135 | 26.5 | 8548 |
| E2 | P5 | 10.7 | 70.0 | 30.0 | 6.0 | 244 | 45.6 | 14710 |
| E2 | P6 | 5.9 | 70.0 | 30.0 | 15.0 | 153 | 51.9 | 16742 |
| C1 | P7 | 27.4 | 70.0 | 30.0 | 1.0 | 193 | 14.1 | 3810 |
| C1 | P8 | 30.2 | 70.0 | 30.0 | 6.0 | 337 | 22.3 | 6027 |
| C1 | P9 | 28.6 | 70.0 | 30.0 | 15.0 | 407 | 28.5 | 7702 |
| C2 | P10 | 27.7 | 70.0 | 30.0 | 1.0 | 103 | 7.4 | 1947 |
| C2 | P11 | 31.1 | 70.0 | 30.0 | 6.0 | 179 | 11.5 | 3026 |
| C2 | P12 | 27.7 | 70.0 | 30.0 | 15.0 | 206 | 14.9 | 3548 |

TABLE 3

Polymer analyses

| Catalyst | Exp. | MFR$_2$ (g/10 min) | MFR$_{21}$ (g/10 min) | M$_w$ exp. (kg/mol) | MWD | T$_m$ (°C.) | T$_c$ (°C.) | XS (%) |
|---|---|---|---|---|---|---|---|---|
| E1 | P1  | —    | 2.0  | 1171 | 2.4 | 144.7 | 105.7 | 0.3 |
| E1 | P2  | 0.8  | 64.0 | 474  | 2.6 | nd    | 105.3 | 0.2 |
| E1 | P3  | 7.5  | —    | 258  | 2.4 | 145.4 | 108.2 | 0.4 |
| E2 | P4  | —    | 2.3  | 1024 | 2.2 | 146.6 | 104.1 | nd  |
| E2 | P5  | 1.1  | —    | 403  | 2.4 | 146.9 | 106.4 | nd  |
| E2 | P6  | 23.2 | —    | 183  | 2.3 | 146.5 | 108.4 | nd  |
| C1 | P7  | 0.1  | 12.5 | 665  | 2.5 | 149.4 | 109.5 | nd  |
| E1 | P1  | —    | 2.0  | 1171 | 2.4 | 144.7 | 105.7 | 0.3 |
| C1 | P8  | 1.3  | —    | 416  | 2.1 | 150.6 | 109.9 | nd  |
| C1 | P9  | 12.3 | —    | 222  | 2.4 | 151.0 | 112.1 | nd  |
| C2 | P10 | 0.1  | —    | 760  | 2.2 | 153.1 | 106.4 | nd  |
| C2 | P11 | 0.6  | —    | 465  | 2.2 | 149.9 | 109.5 | nd  |
| C2 | P12 | —    | —    | 224  | 2.5 | 150.4 | 101.2 | nd  | nd = not determined

TABLE 4

$^{13}$C NMR analyses

| Catalyst | Exp. | mm % | 2.1e % |
|---|---|---|---|
| E1 | P1  | 99.5 | 1.6 |
| E1 | P2  | 99.7 | 1.5 |
| E1 | P3  | 99.6 | 1.5 |
| C2 | P12 | 99.0 | 1.0 |

TABLE 5

Copolymerisation with ethylene

| Catalyst | Exp. | Catalyst (mg) | Temp. (°C.) | Time (min.) | H$_2$ (mmol) | C$_2$ feed (g) | Polymer (g) | Activity (kg/g/h) | Metal activity (kg/g Zr/h) |
|---|---|---|---|---|---|---|---|---|---|
| E1 | P13 | 6.3  | 70.0 | 30.0 | 6.0 | 20.0 | 120 | 38.1 | 11545 |
| E1 | P14 | 8.0  | 70.0 | 30.0 | 6.0 | 40.0 | 98  | 23.4 | 7091  |
| E1 | P15 | 9.0  | 70.0 | 30.0 | 6.0 | 50.0 | 82  | 18.2 | 5515  |
| E2 | P16 | 7.4  | 70.0 | 30.0 | 6.0 | 20.0 | 155 | 41.9 | 13156 |
| E2 | P17 | 11.9 | 70.0 | 30.0 | 6.0 | 40.0 | 167 | 28.1 | 9065  |
| E2 | P18 | 12.0 | 70.0 | 30.0 | 6.0 | 50.0 | 123 | 20.5 | 6613  |

TABLE 6

Propylene/ethylene random copolymers analyses

| Cat | Polymn | C$_2$ feed (g) | MFR$_{21}$ (g/10 min) | M$_w$ exp. (kg/mol) | MWD | T$_m$ (°C.) | T$_c$ (°C.) | C2 content (NMR - wt-%) | XS (%) |
|---|---|---|---|---|---|---|---|---|---|
| E1 | P2  | 0.0  | 64.0 | 474.0 | 2.6 | nd    | 105.3 | 0.0 | 0.2 |
| E1 | P13 | 20.0 | 27.0 | 564.0 | 2.7 | 133.2 | 94.4  | 2.7 | 0.4 |
| E1 | P14 | 40.0 | 18.0 | 618.0 | 2.5 | 121.0 | 85.0  | 4.1 | 0.4 |
| E1 | P15 | 50.0 | 16.0 | 627.0 | 2.8 | 103.0 | 78.5  | 4.6 | nm  |

TABLE 7

Propylene/ethylene random copolymers analyses

| Cat | Polymn | C$_2$ feed (g) | MFR$_2$ (g/10 min) |
|---|---|---|---|
| E2 | P5  | 0.0  | 1.1 |
| E2 | P16 | 20.0 | 0.5 |
| E2 | P17 | 40.0 | 0.2 |
| E2 | P18 | 50.0 | 0.2 |

TABLE 8

Homopolymerisation examples of the invention in comparison with C1 to C4 and examples of WO2009/054832.

| Catalyst | Exp. | H$_2$ (mmol) | Pol time/min | T$_m$ (°C.) | Mw kg/mol | Activity (kg/g/h) |
|---|---|---|---|---|---|---|
| E1 | P1 | 1.0 | 30 | 144.7 | 1171 | 24.5 |
| E1 | P2 | 6.0 | 30 | nd | 474 | 48.8 |
| E1 | P3 | 15.0 | 30 | 145.4 | 258 | 59.5 |
| E2 | P4 | 1.0 | 30 | 146.6 | 1024 | 26.5 |
| E2 | P5 | 6.0 | 30 | 146.9 | 403 | 45.6 |
| E2 | P6 | 15.0 | 30 | 146.5 | 183 | 51.9 |
| C1 | P7 | 1.0 | 30 | 149.4 | 665 | 14.1 |
| C1 | P8 | 6.0 | 30 | 150.6 | 416 | 22.3 |
| C1 | P9 | 15.0 | 30 | 151.0 | 222 | 28.5 |
| C2 | P10 | 1.0 | 30 | 153.1 | 760 | 7.4 |
| C2 | P11 | 6.0 | 30 | 149.9 | 465 | 11.5 |
| C2 | P12 | 15.0 | 30 | 150.4 | 224 | 14.9 |
| D2/mc1 | PolyEx1 | 0 | 60 | 151 | 864 | 7.8 |
| D2/mc1 | PolyEx2 | 50 mg | 60 | 151 | 235 | 19.9 |
| D2/mc2 | PolyEx14 | 0 | 60 | 150 | 1311 | 1.4 |
| D2/mc2 | PolyEx15 | 50 mg | 60 | 150 | 271 | 4.2 |
| D2/mc3 | PolyEx20 | 0 | 60 | 150 | 652 | 3.5 |
| D2/mc3 | PolyEx21 | 50 mg | 60 | 150 | 191 | 10.2 |
| D2/mc4 | PolyEx23 | 0 | 60 | 152 | 709 | 3.0 |
| D2/mc4 | PolyEx24 | 50 mg | 60 | 151 | 208 | 10.2 |
| D2/mc5 | PolyEx26 | 0 | 60 | 151 | 763 | 4.0 |
| D2/mc5 | PolyEx27 | 50 mg | 60 | 150 | 172 | 17.5 |
| D2/mc6 | PolyEx29 | 0 | 60 | 152 | 920 | 4.2 |
| D2/mc6 | PolyEx30 | 50 mg | 60 | 153 | 241 | 17.5 |
| D2/mc7 | PolyEx32 | 0 | 60 | 150 | 812 | 6.0 |
| D2/mc7 | PolyEx33 | 50 mg | 60 | 151 | 225 | 18.3 |
| C3/mcZ | P13 | 1 | 30 | 155.9 | 723 | 33 |
| C3/mcZ | P14 | 6 | 30 | 155.6 | 329 | 109 |
| C3/mcZ | P15 | 15 | 30 | 155.4 | 164 | 143 |
| C4/mcY | P16 | 1 | 30 | 155.7 | 899 | 28 |
| C4/mcY | P17 | 6 | 30 | 156.2 | 300 | 105 |
| C4/mcY | P18 | 15 | 30 | 155.6 | 158 | 161 |

E1: mc is rac-Dimethylsilylene-bis(6-tert-butyl-2-isobutyl-5-methoxy-4-phenyl-1H-inden-1-yl)zirconium dichloride
E2: mc is rac-Dimethylsilylene-bis(6-tert-butyl-2-(2,2-dimethylpropyl)-5-methoxy-4-phenyl-1H-inden-1-yl)zirconium dichloride
Mc1 rac-dimethylsilanediyl-bis-(2-cyclohexylmethyl)-4-(4'-tertbutyl-1-indenyl zirconium dichloride
Mc2 rac-dimethylsilanediyl-bis-(2-cyclohexylmethyl)-4-(1-naphthyl)-1-indenyl zirconium dichloride
Mc3 rac-dimethylsilanediyl-bis-(2-cyclohexylmethyl)-4-(4'methylphenyl)-1-indenyl zirconium dichloride
Mc4 rac-dimethylsilanediyl-bis-(2-cyclohexylmethyl)-4-(3',5'-dimethylphenyl)-1-indenyl zirconium dichloride
Mc5 rac-dimethylsilanediyl-bis-(2-tertbutylmethyl)-4-(4'-tertbutylphenyl)-1-indenyl zirconium dichloride
Mc6 rac-dimethylsilanediyl-bis-(2-(1-adamantylmethyl)-4-(4'tertbutylphenyl)-1-indenyl-zirconium dichloride
Mc7 (Methyl)(n-propyl)silanediyl-bis-(2-(cyclohexylmethyl)-4-(4'-tertbutylphenyl)-1-indenyl) zirconium dichloride
mcZ: rac-1,1'-dimethylsilylene-bis[2-isobutyl-4-(4-tert-butylphenyl)-5,6,7-trihydro-s-indacen-1-yl] zirconium dichloride
mcY: rac-1,1'-dimethylsilylene-bis[2-cyclohexylmethyl)-4-(4-tert-butylphenyl)-5,6,7-trihydro-s-indacen-1-yl] zirconium dichloride
D2/mc examples are derived directly from WO2009/054832. In all these metallocenes there is an alkyl group with beta-branching at position 2 and a phenyl group substituted with one or more alkyl groups at position 4. None of the metallocenes in D2 contain any alkoxy-group as in the present case. Catalysts of D2/mc are supported on silica.

C3 and C4 Comparative Examples

The metallocenes mcZ and mcY are substituted at position 2 with alkyl groups with beta-branching. At position 4, substituted phenyls are present. No alkoxy groups at 5 position are present as in the present case. Catalysts of McZ and McY are prepared using the concept as in the present application, i.e. no external carrier, but prepared by emulsion-solidification method. Homopolymerisation of propylene was carried out as above. For completeness, the following additional data is provided:

| Catalyst | Al (%) | Zr (%) | Al/Zr (molar) |
|---|---|---|---|
| C3 | 26.1 | 0.33 | 267 |
| C4 | 21.4 | 0.23 | 314 |

| Exp. | Catalyst | Catalyst (mg) | H$_2$ (mmol) |
|---|---|---|---|
| P13 | CE3 | 8.1 | 1 |
| P14 |  | 7.0 | 6 |
| P15 |  | 6.0 | 15 |
| P16 | CE4 | 7.1 | 1 |
| P17 |  | 7.0 | 6 |
| P18 |  | 6.0 | 15 |

Note on the Amount of Hydrogen

In comparative examples C3 and C4 as well in the present application the amount of hydrogen is 1.0/6.0/15.0 mmol, i.e. the Ratio hydrogen/propylene (wt/wt) in the present case as well in C3 and C4 is 2 mg (1 mmol)/1100 mg=0.002; 12 mg (6 mmol)/1100 mg=0.011; 30 mg (15 mmol)/1100 mg=0.027

In examples of D2 the amount of hydrogen used in polymerisation is 0 or 50 mg. Ratio H2/propylene (wt/wt) in D2 examples is 0 or 50 mg/1837 mg=0.027 i.e. Polyemerisations where 1 (=close 0) or 15 mmol hydrogen are used are comparable with examples of WO2009054832 in this respect.

Conclusions:

It can be seen from the above table that in examples of the invention, when hydrogen is 0 (or 1 mmol)—Tm is lower in all cases, Mw is higher AND the activity is better compared to any of the examples as shown for comparison (except for D2/PolyEx 14, where Mw is higher, but the activity is very low).

When hydrogen is 15 mmol or 50 mg, Tm is lower in all cases, Mw is higher AND/OR the activity is better compared to any of the examples as shown for comparison. Based on the above it can be clearly seen that the effect of using metallocenes having both beta-branched alkyl group at position 2, and also an alkoxy group at 5-position results desired effects as disclosed in the present application i.e.

high activity catalysts
high Mw polymers
polymers with low Tm

Thus, catalysts prepared from complexes as claimed in claim 1 are novel and inventive over prior art.

The invention claimed is:
1. A solid, particulate catalyst comprising:
(i) a complex of formula (I):

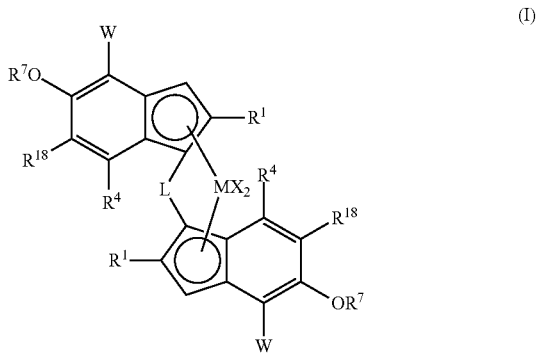

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, or —R'$_2$Ge—, wherein each R' is independently a hydrogen atom, C1-C20-hydrocarbyl, tri(C1-C20-alkyl)silyl, C6-C20-aryl, C7-C20-arylalkyl or C7-C20-alkylaryl;

each $R^1$ is a C4-C20 hydrocarbyl radical branched at the β-atom to the cyclopentadienyl ring, optionally containing one or more heteroatoms belonging to groups 14-16, or is a C3-C20 hydrocarbyl radical branched at the β-atom to the cyclopentadienyl ring where the β-atom is an Si-atom;

each $R^{18}$ is a C1-C20 hydrocarbyl radical optionally containing one or more heteroatoms belonging to groups 14-16;

each $R^4$ is a hydrogen atom or a $C_{1-6}$-hydrocarbyl radical;

each W is a 5 or 6 membered aryl or heteroaryl ring wherein each atom of said ring is optionally substituted with at least one $R^5$ group;

each $R^5$ is the same or different and is a C1-C20 hydrocarbyl radical optionally containing one or more heteroatoms belonging to groups 14-16; and optionally two adjacent $R^5$ groups taken together form a further mono or multicyclic ring condensed to W; and each $R^7$ is a C1-C20 hydrocarbyl radical;

and (ii) a cocatalyst, preferably comprising an organometallic compound of a Group 13 metal.

2. A catalyst as claimed in claim 1 wherein the catalyst is obtained by a process in which (I) a liquid/liquid emulsion system is formed, said liquid/liquid emulsion system comprising a solution of the catalyst components (i) and (ii) dispersed in a solvent so as to form dispersed droplets; and (II) solid particles are formed by solidifying said dispersed droplets.

3. A catalyst as claimed in claim 1, wherein the catalyst further comprises an inert carrier.

4. A catalyst as claimed in claim 1 wherein in said complex of formula (I), L is —$SiR^6_2$—, wherein each $R^6$ is independently C1-C20-alkyl, C6-C20-aryl or tri(C1-C20-alkyl)silyl-residue or ethylene bridge.

5. A catalyst as claimed in claim 1 wherein in said complex of formula (I) $R^1$ is the group —$CH_2$—$R^{1\prime\prime}$ and $R^{1\prime\prime}$ represents a C3-19 hydrocarbyl group optionally containing one or more heteroatoms belonging to groups 14-16 or is a C2-19 hydrocarbyl group where the β-atom to the cyclopentadienyl ring is an Si-atom, so as to provide a branch β to the cyclopentadienyl ring.

6. A catalyst as claimed in claim 1 wherein $R^7$ is C1-6 alkyl.

7. A catalyst as claimed in claim 1 wherein $R^{18}$ is C3-10 alkyl.

8. A catalyst as claimed in claim 1 wherein in said complex of formula (I) W is an optionally substituted phenyl group, or a 5 or 6 membered heteroaryl group selected from furanyl, thiophenyl, pyrrolyl, triazolyl, or pyridinyl.

9. A catalyst as claimed in claim 1 wherein in said complex of formula (I) $R^5$ is a linear or branched, cyclic or acyclic, C1-C10-alkyl group or two adjacent $R^5$ groups taken together form a further mono or multicyclic aromatic ring condensed to W.

10. A catalyst as claimed in claim 1 wherein said catalyst comprises a complex of formula (II):

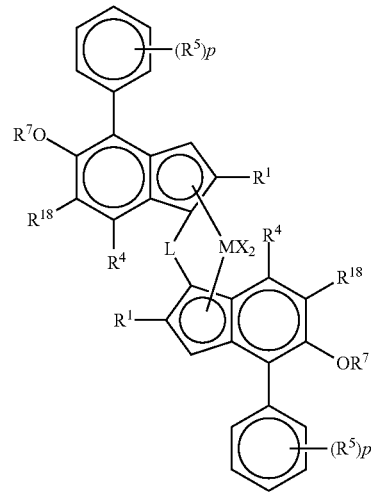

(II)

wherein
M is Zr or Hf;
each $R^1$ is $CH_2$—Ph or $CH_2$—$C(R^3)_{3-q}(H)_q$ wherein $R^3$ is a $C_{1-6}$-alkyl group or together two $R^3$ groups form a $C_{3-7}$-cycloalkyl ring wherein said ring is optionally substituted by a $C_{1-6}$ alkyl group and q is 1 or 0;
L is $SiR^6_2$;
$R^6$ is C1-10 alkyl, $C_{6-10}$-aryl, $C_{7-12}$-alkylaryl, or $C_{7-12}$-arylalkyl;
each X is a hydrogen atom, benzyl, OR, a halogen atom, or an R group;
R is $C_{1-10}$ alkyl or $C_{6-20}$-aryl;
each $R^4$ is H or $C_{1-3}$-alkyl;
p is 0 to 2;
$R^5$ is $C_{1-10}$-alkyl;
$R^7$ is $C_{1-10}$ alkyl; and
$R^{18}$ is $C_{1-10}$-alkyl;
and wherein the two ligands forming the complex are identical.

11. A catalyst as claimed in claim 1 wherein said catalyst comprises a complex of formula (III)

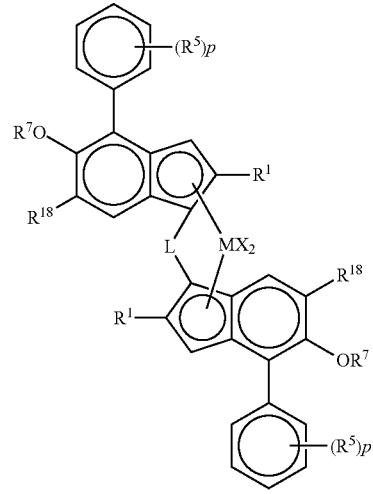

(III)

in which:
M is Zr;
each $R^1$ is $CH_2$—Ph or $CH_2$—$C(R^3)_{3-q}(H)_q$ wherein $R^3$ is a $C_{1-6}$-alkyl group or together two $R^3$ groups form a $C_{3-7}$-cycloalkyl ring wherein said ring is optionally substituted by a $C_{1-6}$ alkyl group and q is 1 or 0;

L is SiR$^6_2$;
R$^6$ is C$_{1-8}$ alkyl;
each X is a halogen atom, methoxy, benzyl or methyl;
p is 0 or 1;
R$^7$ is C$_{1-6}$ alkyl;
R$^{18}$ is C$_{3-10}$ alkyl; and
R$^5$ is C1-6 alkyl;
and wherein the two ligands forming the complex are identical.

12. A catalyst as claimed claim 1 wherein said catalyst comprises a complex of formula (IV)

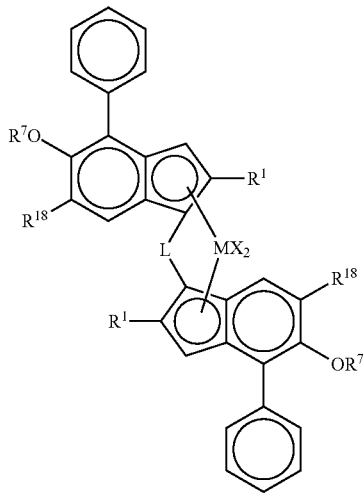

(IV)

wherein L is SiR$^6_2$;
R$^6$ is C$_{1-8}$ alkyl;
R$^1$ is CH$_2$—Ph or CH$_2$—C(R$^3$)$_{3-q}$(H)$_q$ wherein R$^3$ is a C$_{1-6}$-alkyl group or together two R$^3$ groups form a C$_{3-7}$-cycloalkyl ring wherein said ring is optionally substituted by a C$_{1-6}$ alkyl group and q is 1 or 0;
each X is a halogen atom, methoxy, benzyl or methyl;
M is Zr;
R$^7$ is C$_{1-6}$ alkyl; and
R$^{18}$ is C$_{3-10}$ alkyl;
and wherein the two ligands forming the complex are identical.

13. A catalyst as claimed in claim 1 wherein said catalyst comprises a complex of formula (VI) or (VII)

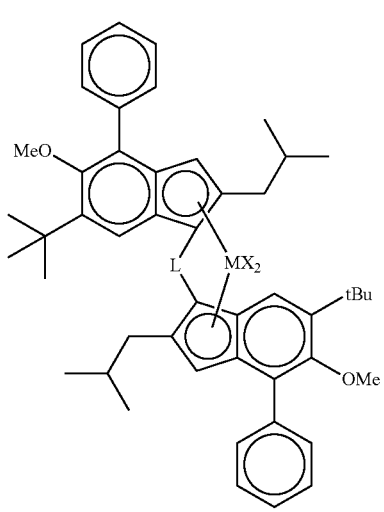

(VI)

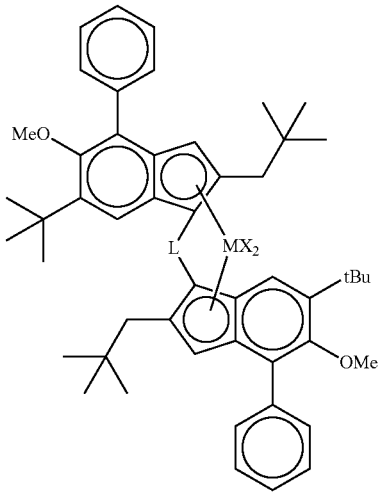

(VII)

wherein M is Zr or Hf;
L is SiR$^6_2$;
R$^6$ is C1-10 alkyl, C$_{6-10}$-aryl, C$_{7-12}$-alkylaryl, or C$_{7-12}$-arylalkyl;
each X is a hydrogen atom, benzyl, OR, a halogen atom, or an R group; and
R is C$_{1-10}$ alkyl or C$_{6-20}$ aryl.

14. A process for manufacture of a catalyst as claimed in claim 1 comprising
obtaining a complex of formula (I) and a cocatalyst as hereinbefore described;
forming a liquid/liquid emulsion system, which comprises a solution of catalyst components (i) and (ii) dispersed in a solvent, and solidifying said dispersed droplets to form solid particles.

15. A process for polymerisation of at least one olefin comprising reacting said at least one olefin with a catalyst as claimed in claim 1.

16. A complex of formula (VI) or (VII)

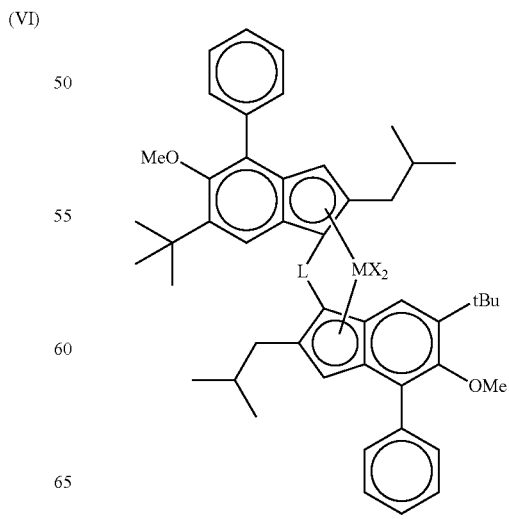

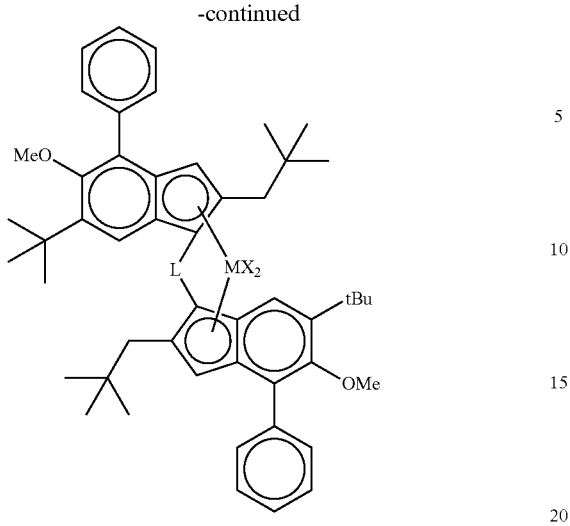
wherein M is Zr or Hf;
L is $SiR^6_2$;
$R^6$ is C1-10 alkyl, $C_{6-10}$-aryl, $C_{7-12}$-alkylaryl, or $C_{7-12}$-arylalkyl;
each X is a hydrogen atom, benzyl, OR, a halogen atom, or an R group; and
R is $C_{1-10}$ alkyl or $C_{6-20}$ aryl.
* * * * *